United States Patent
Zhang et al.

(10) Patent No.: US 11,229,680 B2
(45) Date of Patent: Jan. 25, 2022

(54) AUTOPHAGY INHIBITORS

(71) Applicant: The Hong Kong University of Science and Technology, Hong Kong (CN)

(72) Inventors: Mingjie Zhang, Hong Kong (CN); Jianchao Li, Sai Kung (CN); Ruichi Zhu, Hong Kong (CN); Chao Wang, Anhui (CN)

(73) Assignee: The Hong Kong University of Science and Technology, Kowloon (HK)

( * ) Notice: Subject to any disclaimer, the term of this patent is extended or adjusted under 35 U.S.C. 154(b) by 0 days.

(21) Appl. No.: 16/629,276

(22) PCT Filed: Nov. 5, 2018

(86) PCT No.: PCT/CN2018/113894
§ 371 (c)(1),
(2) Date: Jan. 7, 2020

(87) PCT Pub. No.: WO2019/096018
PCT Pub. Date: May 23, 2019

(65) Prior Publication Data
US 2021/0169980 A1    Jun. 10, 2021

Related U.S. Application Data

(60) Provisional application No. 62/707,656, filed on Nov. 14, 2017.

(51) Int. Cl.
| | |
|---|---|
| *A61K 38/16* | (2006.01) |
| *C07K 14/00* | (2006.01) |
| *A61K 38/17* | (2006.01) |
| *C07K 14/47* | (2006.01) |

(52) U.S. Cl.
CPC ...... *A61K 38/1761* (2013.01); *C07K 14/4747* (2013.01)

(58) Field of Classification Search
CPC .... A61K 38/16; A61K 38/1761; C07K 14/00; C07K 14/4747
See application file for complete search history.

(56) References Cited

U.S. PATENT DOCUMENTS

| | | | |
|---|---|---|---|
| 2007/0015145 A1* | 1/2007 | Woolf | C12N 9/16 435/6.16 |
| 2016/0166636 A1 | 6/2016 | Muller et al. | |

FOREIGN PATENT DOCUMENTS

| | | |
|---|---|---|
| CN | 102643350 A | 8/2012 |
| CN | 104211765 A | 12/2014 |
| CN | 107501405 A | 12/2017 |

OTHER PUBLICATIONS

UniProt O70511, pp. 1-17. Integrated into UniProtKB/Swiss-Prot on Jul. 9, 2014. (Year: 2014).*
SEQ ID No. 1325 from U.S. 20070015145, pp. 1-6. 2007. (Year: 2007).*
International Search Report in PCT/CN2018/113894, dated Feb. 12, 2019, 5 pages.

* cited by examiner

*Primary Examiner* — Julie Ha
(74) *Attorney, Agent, or Firm* — Kilpatrick Townsend & Stockton LLP

(57) ABSTRACT

Provided herein are recombinant peptides useful for inhibiting the function of autophagy-related 8 (Atg8) proteins. The recombinant peptides can be used in the preparation of imaging agents for monitoring autophagy in a cell or subject and treating autophagy related diseases, such as cancer.

17 Claims, 23 Drawing Sheets
Specification includes a Sequence Listing.

C

| AnkB | GABARAP | $K_d$ (nM) | Fold changes | LC3A | $K_d$ (nM) | Fold changes |
|---|---|---|---|---|---|---|
| WT | WT | 0.27±0.05 | 1 | WT | 3.6±0.3 | 1 |
| W1592R | WT | >100000 | >3.7E5 | WT | ~26600 | ~7400 |
| E1599R | WT | 38±9 | ~140 | WT | 312±29 | ~87 |
| WT | R67E | 56±15 | ~210 | R70E | 860±58 | ~240 |

AnkB $^{1588}$ VEEE(WR)R VIVSDEEIEEARQKAPLEITEY$^{1614}$  AnkG $^{1985}$ PEDD(WR)(ER)R,R TE/SSEEIREARQAAASHAPS$^{2010}$

B

| $K_d$ (nM) | AnkB WT | AnkB WR negative control | AnkG WT | AnkG ER | AnkG WR negative control |
|---|---|---|---|---|---|
| GABARAP | 0.34±0.05 | >100000 | 2.6±0.7 | 6.9±0.6 | ~10800 |
| LC3B | 4.2±1.2 | ~28810 | 339±0.05 | ~11060 | ND |
| LGG-1 | 1.2±0.4 | ~8330 | 1.6±0.5 | 8.5±0.7 | ND |
| LGG-2 | 98±13 | ~82800 | 210±13 | 8470±310 | ND |

Figure 6

SEQUENCE LISTING

```
<160> NUMBER OF SEQ ID NOS: 43

<210> SEQ ID NO 1
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: AnkG rat recombinant peptide, prepared in the
      lab

<400> SEQUENCE: 1

Pro Glu Asp Asp Trp Thr Glu Phe Ser Ser Glu Glu Ile Arg Glu Ala
1               5                   10                  15

Arg Gln Ala Ala Ala Ser His Ala Pro Ser
            20                  25

<210> SEQ ID NO 2
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: AnkG E1991R rat recombinant peptide, prepared
      in the lab

<400> SEQUENCE: 2

Pro Glu Asp Asp Trp Thr Arg Phe Ser Ser Glu Glu Ile Arg Glu Ala
```

Arg Gln Ala Ala Ala Ser His Ala Pro Ser
            20                  25

<210> SEQ ID NO 3
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: AnkB human recombinant peptide, prepared in the
      lab

<400> SEQUENCE: 3

Val Glu Glu Glu Trp Val Ile Val Ser Asp Glu Glu Ile Glu Glu Ala
1               5                   10                  15

Arg Gln Lys Ala Pro Leu Glu Ile Thr Glu Tyr
            20                  25

<210> SEQ ID NO 4
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: AnkG human recombinant peptide, prepared in the
      lab

<400> SEQUENCE: 4

Pro Glu Asp Asp Trp Ile Glu Phe Ser Ser Glu Glu Ile Arg Glu Ala
1               5                   10                  15

Arg Gln Gln Ala Ala Ala Ser Gln Ser Pro Ser
            20                  25

<210> SEQ ID NO 5
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: AnkG chicken recombinant peptide, prepared in
      the lab

<400> SEQUENCE: 5

Ser Glu Asp Asp Trp Val Glu Phe Ser Thr Glu Glu Ile Asp Glu Ala
1               5                   10                  15

Arg Gln Gln Ala Leu Thr Ser Pro Pro Met Ser
            20                  25

<210> SEQ ID NO 6
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: AnkG xenopus tropicalis recombinant peptide,
      prepared in the lab

<400> SEQUENCE: 6

```
Pro Glu Asp Glu Trp Val Glu Phe Ser Asn Glu Glu Leu Glu Glu Ala
1               5                   10                  15

Arg Gln Leu Ala Asn Thr His Ala Pro
            20                  25
```

```
<210> SEQ ID NO 7
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: AnkG zebra fish recombinant peptide, prepared
      in the lab

<400> SEQUENCE: 7
```

```
Ser Glu Asp Glu Trp Glu Glu Phe Ser Lys Asp Glu Ile Glu Glu Ala
1               5                   10                  15

Arg His Ser Ala Leu Arg Ser Leu Pro Thr
            20                  25
```

```
<210> SEQ ID NO 8
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: AnkB mouse recombinant peptide, prepared in the
      lab

<400> SEQUENCE: 8
```

```
Leu Glu Glu Glu Trp Val Ile Val Ser Asp Glu Glu Ile Gln Glu Ala
1               5                   10                  15

Lys Gln His Ala Pro Val Glu Ile Asp Glu His
            20                  25
```

```
<210> SEQ ID NO 9
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: AnkB chicken recombinant peptide, prepared in
      the lab

<400> SEQUENCE: 9
```

```
Val Glu Glu Glu Trp Val Ile Val Ser Asp Glu Glu Ile Glu Glu Ala
1               5                   10                  15

Arg Arg Asn Ala Pro Val Glu Val Thr Glu Pro
            20                  25
```

```
<210> SEQ ID NO 10
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: AnkB zebra fish recombinant peptide, prepared
      in the lab

<400> SEQUENCE: 10
```

```
Lys Asp Glu Glu Trp Val Leu Leu Thr Glu Ser Glu Ile Glu Glu Ala
1               5                   10                  15

Lys Met Met Ala Ala Phe Glu Ser Gln Glu Ala
            20                  25

<210> SEQ ID NO 11
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: AnkB W1592R human recombinant peptide, prepared
      in the lab

<400> SEQUENCE: 11

Val Glu Glu Glu Arg Val Ile Val Ser Asp Glu Ile Glu Glu Ala
1               5                   10                  15

Arg Gln Lys Ala Pro Leu Glu Ile Thr Glu Tyr
            20                  25

<210> SEQ ID NO 12
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: AnkB E1599R human recombinant peptide, prepared
      in the lab

<400> SEQUENCE: 12

Val Glu Glu Glu Trp Val Ile Val Ser Asp Glu Arg Ile Glu Glu Ala
1               5                   10                  15

Arg Gln Lys Ala Pro Leu Glu Ile Thr Glu Tyr
            20                  25

<210> SEQ ID NO 13
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: AnkG W1989R rat recombinant peptide, prepared
      in the lab

<400> SEQUENCE: 13

Pro Glu Asp Asp Arg Thr Glu Phe Ser Ser Glu Glu Ile Arg Glu Ala
1               5                   10                  15

Arg Gln Ala Ala Ala Ser His Ala Pro Ser
            20                  25

<210> SEQ ID NO 14
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: AnkG E1996R rat recombinant peptide, prepared
      in the lab
```

```
<400> SEQUENCE: 14

Pro Glu Asp Asp Trp Thr Glu Phe Ser Ser Glu Arg Ile Arg Glu Ala
1               5                   10                  15

Arg Gln Ala Ala Ala Ser His Ala Pro Ser
            20                  25

<210> SEQ ID NO 15
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: AnkG I1997Q rat recombinant peptide, prepared
      in the lab

<400> SEQUENCE: 15

Pro Glu Asp Asp Trp Thr Glu Phe Ser Ser Glu Gln Arg Glu Ala
1               5                   10                  15

Arg Gln Ala Ala Ala Ser His Ala Pro Ser
            20                  25

<210> SEQ ID NO 16
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: AnkG A2000Q rat recombinant peptide, prepared
      in the lab

<400> SEQUENCE: 16

Pro Glu Asp Asp Trp Thr Glu Phe Ser Ser Glu Glu Ile Arg Glu Gln
1               5                   10                  15

Arg Gln Ala Ala Ala Ser His Ala Pro Ser
            20                  25

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: AnkG rat recombinant alpha helix, prepared in
      lab

<400> SEQUENCE: 17

Ile Arg Glu Ala Arg Gln Ala
1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: AnkB human recombinant alpha helix, prepared in
      lab

<400> SEQUENCE: 18
```

Ile Glu Glu Ala Arg Gln Lys Ala
1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: AnkG human recombinant alpha helix

<400> SEQUENCE: 19

Ile Arg Glu Ala Arg Gln Gln Ala
1               5

<210> SEQ ID NO 20
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: FYCO1 recombinant human sequence, prepared in
      lab

<400> SEQUENCE: 20

Asp Asp Ala Val Phe Asp Ile Ile Thr Asp Glu Glu Leu Cys Gln Ile
1               5                   10                  15

Gln Glu Ser Gly Ser Ser Leu Pro Glu Thr
            20                  25

<210> SEQ ID NO 21
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: FAM134B recombinant human sequence, prepared in
      lab

<400> SEQUENCE: 21

Glu Gly Asp Asp Phe Glu Leu Leu Asp Gln Ser Glu Leu Asp Gln Ile
1               5                   10                  15

Glu Ser Glu Leu Gly Leu Thr Gln Asp Gln
            20                  25

<210> SEQ ID NO 22
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: (GGGS)n peptide linker, prepared in the lab
<220> FEATURE:
<221> NAME/KEY: SITE
<222> LOCATION: (1)..(40)
<223> OTHER INFORMATION: This sequence may encompass 1-10 "Gly Gly Gly
      Ser" repeating units

<400> SEQUENCE: 22

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser
        35                  40

<210> SEQ ID NO 23
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: (GGSG)n peptide linker, prepared in lab
<220> FEATURE:
<221> NAME/KEY: SITE
<222> LOCATION: (1)..(40)
<223> OTHER INFORMATION: This sequence may encompass 1-10 "Gly Gly Ser
      Gly" repeating units

<400> SEQUENCE: 23

Gly Gly Ser Gly Gly Gly Ser Gly Gly Gly Ser Gly Gly Gly Ser Gly
1               5                   10                  15

Gly Gly Ser Gly Gly Gly Ser Gly Gly Gly Ser Gly Gly Gly Ser Gly
            20                  25                  30

Gly Gly Ser Gly Gly Gly Ser Gly
        35                  40

<210> SEQ ID NO 24
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: (GGGGS)n peptide linker, prepared in lab
<220> FEATURE:
<221> NAME/KEY: SITE
<222> LOCATION: (1)..(50)
<223> OTHER INFORMATION: This sequence may encompass 1-10 "Gly Gly Gly
      Gly Ser" repeating units

<400> SEQUENCE: 24

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser
    50

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: SGLRSGS peptide linker, prepared in the lab

<400> SEQUENCE: 25

Ser Gly Leu Arg Ser Gly Ser
1               5

```
<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: YSDLDGS peptide linker, prepared in the lab

<400> SEQUENCE: 26

Tyr Ser Asp Leu Asp Gly Ser
1               5

<210> SEQ ID NO 27
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(20)
<223> OTHER INFORMATION: This sequence may encompass 1-10 "Gly Ser"
      repeating units

<400> SEQUENCE: 27

Gly Ser Gly Ser Gly Ser Gly Ser Gly Ser Gly Ser Gly Ser Gly Ser
1               5                   10                  15

Gly Ser Gly Ser
            20

<210> SEQ ID NO 28
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(30)
<223> OTHER INFORMATION: This sequence may encompass 1-10 "Gly Gly Ser"
      repeating units

<400> SEQUENCE: 28

Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Gly Ser
            20                  25                  30

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(10)
<223> OTHER INFORMATION: This sequence may encompass 1-10 residues

<400> SEQUENCE: 29

Gly Gly Gly Gly Gly Gly Gly Gly Gly Gly
1               5                   10
```

```
<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(8)
<223> OTHER INFORMATION: This sequence may encompass 1-4 "Gly Ser"
      repeating units

<400> SEQUENCE: 30

Gly Ser Gly Ser Gly Ser Gly Ser
1               5

<210> SEQ ID NO 31
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(16)
<223> OTHER INFORMATION: This sequence may encompass 1-4 "Gly Gly Gly
      Ser" repeating units

<400> SEQUENCE: 31

Gly Gly Gly Ser Gly Gly Gly Ser Gly Gly Gly Ser Gly Gly Gly Ser
1               5                   10                  15

<210> SEQ ID NO 32
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(16)
<223> OTHER INFORMATION: This sequence may encompass 1-4 "Gly Gly Ser
      Gly" repeating units

<400> SEQUENCE: 32

Gly Gly Ser Gly Gly Gly Ser Gly Gly Gly Ser Gly Gly Gly Ser Gly
1               5                   10                  15

<210> SEQ ID NO 33
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(20)
<223> OTHER INFORMATION: This sequence may encompass 1-4 "Gly Gly Gly
      Gly Ser" repeating units

<400> SEQUENCE: 33

Gly Gly Gly Gly Ser Gly Gly Gly Ser Gly Gly Gly Gly Ser Gly
1               5                   10                  15

Gly Gly Gly Ser
            20
```

```
<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(12)
<223> OTHER INFORMATION: This sequence may encompass 1-4 "Gly Gly Ser"
      repeating units

<400> SEQUENCE: 34

Gly Gly Ser Gly Gly Ser Gly Gly Ser Gly Gly Ser
1               5                   10

<210> SEQ ID NO 35
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(4)
<223> OTHER INFORMATION: This sequence may encompass 1-4 residues

<400> SEQUENCE: 35

Gly Gly Gly Gly
1

<210> SEQ ID NO 36
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Ser Asp Lys Gly His Ser Pro Glu Asp Asp Trp Ile Glu Phe Ser Ser
1               5                   10                  15

Glu Glu Ile Arg Glu Ala Arg Gln Gln Ala Ala Ala Ser Gln Ser Pro
            20                  25                  30

Ser Leu Pro Glu Arg Val Gln Val Lys Ala
        35                  40

<210> SEQ ID NO 37
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Ser Asp Lys Gly His Ser Pro Glu Asp Asp Trp Thr Glu Phe Ser Ser
1               5                   10                  15

Glu Glu Ile Arg Glu Ala Arg Gln Ala Ala Ser His Ala Pro Ser
            20                  25                  30

Leu Pro Glu Arg Val His Gly Lys Ala
        35                  40

<210> SEQ ID NO 38
```

```
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Ser Asp Gln Gly His Leu Ser Glu Asp Asp Trp Val Glu Phe Ser Thr
1               5                   10                  15

Glu Glu Ile Asp Glu Ala Arg Gln Gln Ala Leu Thr Ser Pro Pro Met
            20                  25                  30

Ser Val Pro Glu Lys Ala Gln Ile Lys Thr
        35                  40

<210> SEQ ID NO 39
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Cys His Ala Gly His Ser Pro Glu Asp Glu Trp Val Glu Phe Ser Asn
1               5                   10                  15

Glu Glu Leu Glu Glu Ala Arg Gln Leu Ala Asn Thr His Ala Pro His
            20                  25                  30

Lys Val Glu Ile Lys Thr
        35

<210> SEQ ID NO 40
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Ser Arg Lys Glu Arg Ala Ser Glu Asp Glu Trp Glu Glu Phe Ser Lys
1               5                   10                  15

Asp Glu Ile Glu Glu Ala Arg His Ser Ala Leu Arg Ser Leu Pro Thr
            20                  25                  30

Phe Glu Ser Thr Leu Pro Val Gly Pro
        35                  40

<210> SEQ ID NO 41
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Lys Glu Glu Glu Trp Val Ile Leu Ser Asp Glu Glu Val Gln Glu Ala
1               5                   10                  15

Lys Leu Asn Ala His Leu Glu Ile Glu Glu Ala
            20                  25

<210> SEQ ID NO 42
<211> LENGTH: 26
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 42

Pro Glu Asp Asp Trp Ile Glu Phe Ser Ser Glu Glu Ile Arg Glu Ala
1               5                  10                  15

Arg Gln Gln Ala Ala Ala Ser Gln Ser Pro
            20                  25

<210> SEQ ID NO 43
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Val Glu Glu Glu Trp Val Ile Val Ser Asp Glu Glu Ile Glu Glu Ala
1               5                  10                  15

Arg Gln Lys Ala Pro Leu Glu Ile Thr Glu
            20                  25
```

AUTOPHAGY INHIBITORS

CROSS-REFERENCE TO RELATED APPLICATIONS

This application is a U.S. National Stage of PCT/CN2018/113894, international filing date Nov. 5, 2018, which claims the benefit of priority of U.S. Provisional Application No. 62/707,656, filed on Nov. 14, 2017, the contents of which being hereby incorporated by reference in their entirety for all purposes.

SEQUENCE LISTING

The instant application contains a Sequence Listing which has been submitted electronically in ASCII format and is hereby incorporated by reference in its entirety. Said ASCII copy, created on Sep. 24, 2021, is named 091256-1172371-002000US_SL.txt and is 18,974 bytes in size.

TECHNICAL FIELD

The present disclosure generally relates to recombinant peptides useful as inhibitors of autophagy-related 8 proteins (Atg8), methods for their preparation, and use of the recombinant peptides as inhibitors of autophagy and/or imaging agents of autophagy.

BACKGROUND

Autophagy, meaning "self-eating" in Greek, is an evolutionarily conserved pathway in eukaryotes first described more than half a century ago. Autophagy is responsible for degrading intracellular protein aggregates, damaged organelles and invasive pathogens thus plays essential roles in maintaining cellular homeostasis as well as responding to stress conditions. Autophagy is a highly regulated process involving multiple steps. First, a cup-shaped membrane called phagophore or isolation membrane nucleates to initiate autophagy. The phagophore continues to elongate and mature into a closed double-membrane autophagosome. The autophagosome later fuses with lysosome to form autolysosome. The materials engulfed inside the autolysosome will then undergo lysosomal degradation and recycling. Dysregulation of autophagy is tightly associated with a variety of human diseases including, but not limited to, cancers, metabolic diseases, immunity disorders and neurodegenerative diseases (Choi et al., 2013; Deng et al., 2017; Galluzzi et al., 2017b; Jiang and Mizushima, 2014; Levine and Kroemer, 2008; Levine et al., 2011; Menzies et al., 2015; Rubinsztein et al., 2012). Accordingly, autophagy has drawn increasing attention as a potential target for therapeutic intervention.

Over the past two to three decades, genetic screenings in yeast and *C. elegans* have enabled researchers to identify and characterize a series of key components of the autophagy machinery, including autophagy-related (Atg) genes and ectopic P-granules (Epg) genes. Among these genes, Atg8 participates in multiple steps of autophagic process and considered as a central component in autophagy. Atg8 is attached to phagophore membrane via conjugation with a phosphatidylethanolamine (PE) lipid. Atg8-PE facilitates phagophore expansion and autophagosome closure, most likely through its membrane tethering and fusion activity. Atg8 also recruits the Atg1/ULK1 complex to the phagophore to promote autophagosome formation. In the closed autophagosome, Atg8 on the outer membrane interacts with Rab effectors PLEKHM1 and EPG5 for fusion with late endosomes/lysosome. In selective autophagy, Atg8 on the inner membrane of phagophore interacts with autophagy receptors (e.g. p62 and NBR1) to recruit targets for degradation. As a result, Atg8 and its orthologues (Atg8s) are commonly used as autophagy indicators, and elimination of Atg8's function impairs autophagy. Yeast contains only one Atg8 gene, but in higher eukaryotes like *C. elegans*, there are two homologs LGG-1 and LGG-2. In vertebrates, these two members further expand into two subfamilies, namely the GABARAP subfamily (GABARAPs, including GABARAP, GABARAPL1, and GABARAPL2) and the LC3 subfamily (LC3s, including LC3A, LC3B, and LC3C). Genetic studies in *C. elegans* and RNA interference in mammalian cells have shown that the two families play some non-redundant roles and neither of them is dispensable for the overall autophagic process. However, the high sequence similarities shared by different mammalian Atg8 homologs and potential genetic compensations in response to gene knockout or knockdown complicate further functional studies of each individual member.

Atg8s contain a short N-terminal two-helix extension followed by a C-terminal ubiquitin-like domain. The two hydrophobic pockets in Atg8s can recognize proteins containing a $\Phi XX\Psi$ motif (where $\Phi$ represents aromatic amino acids Trp/Tyr/Phe, $\Psi$ represents hydrophobic amino acids Leu/Ile/Val and X represents any amino acid), also known as LC3 interacting region (LIR) or Atg8 interacting motif (AIM) (Birgisdottir et al., 2013; Noda et al., 2010). In addition to the two hydrophobic residues, a typical LIR usually contains a few N-terminal acidic residues Asp/Glu and binds to Atg8s with dissociation constants ($K_d$) ranging from micromolar to sub-micromolar. Two recent studies have reported the developments of LIR-based sensors to monitor autophagy using different strategies (Lee et al., 2017; Stolz et al., 2017). However, these LIR-based peptides, like many known canonical naturally occurring LIR motifs, still bind to Atg8s with modest affinities. Due to the central roles of Atg8s in autophagy, it is exceedingly desirable to develop extremely potent and highly selective Atg8 binding peptides as such peptides will be remarkably valuable for numerous applications, such as to efficiently inhibit Atg8-mediated selective autophagy spatiotemporally in living animals, as biochemical tools to study and clearly delineate functions of different Atg8 members in autophagy, and to monitor autophagy process by specifically recognizing each member of Atg8s, etc. In view of the foregoing, there exists a need to develop improved inhibitors of Atg8 proteins.

SUMMARY OF THE INVENTION

The present disclosure relates to recombinant peptides, which can comprise between 22 to 27 residues and are derived from the giant isoforms of a scaffold protein family named ankyrins (270/480 kD ankyrin-G isoform or 440 kD ankyrin-B isoform). The recombinant peptides can be configured to tightly bind to all or a subgroup of Atg8 proteins, including but not limited, to mammalian GABARAP, GABARAPL1, GABARAPL2, LC3A, LC3B, and LC3C and *C. elegans* LGG-1 and LGG-2) with a disassociation constant ($K_d$) in the nanomolar range. Crystallographic studies of the Ank-derived peptides in complex with individual Atg8 family members including GABARAP, GABARAPL1, GABARAPL2, or LC3B showed that the Ank-derived peptides contain both the canonical LIR core ($\Phi XX\Psi$ motif) and an additional C-terminal amphipathic α-helix, which is crucial for the super strong binding. Finally, a consensus sequence motif for certain embodiments of the extended LIRs with super strong Atg8 binding affinities was determined to be: "(D/E)$_{2-3}$X$_{0-2}$ΦXXΨXXXEΨρρΨρρρΨ", wherein Φ represents aromatic residues; Ψ represents aliphatic or aromatic residues; ρ represents polar residues; and X represents any residues.

In a first aspect, provided herein is a recombinant peptide comprising a sequence represented by Formula I:

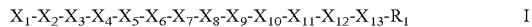   I or a pharmaceutically acceptable salt or zwitterion thereof, wherein $X_1$, $X_2$, and $X_3$, are independently aspartate, glutamate, or absent;

$X_4$ and $X_5$ are independently any amino acid or absent;
$X_6$ is an amino acid having a side chain comprising an aromatic or heteroaromatic moiety;
$X_7$ and $X_8$ are independently any amino acid;
$X_9$ is an amino acid having a side chain comprising an acyclic aliphatic or an aromatic moiety;
$X_{10}$, $X_{11}$, and $X_{12}$ are independently any amino acid;
$X_{13}$ is glutamate or arginine; and
$R_1$ is an amphipathic alpha helix comprising between 7 and 15 amino acids, wherein
at least two of $X_1$, $X_2$, and $X_3$, are selected from aspartate and glutamate.

In a first embodiment of the first aspect, provided herein is the recombinant peptide of the first aspect, wherein $X_7$ and $X_8$ are independently an amino acid having a side chain comprising an alcohol, acyclic aliphatic or a carboxylic acid moiety.

In a second embodiment of the first aspect, provided herein is the recombinant peptide of the first aspect, wherein $X_{10}$, $X_{11}$, and $X_{12}$ are independently an amino acid having a side chain comprising an alcohol, a carboxylic acid, or an amide moiety.

In a third embodiment of the first aspect, provided herein is the recombinant peptide of the first aspect, wherein $R_1$ comprises a sequence represented by Formula II:

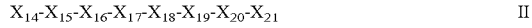   II wherein $X_{14}$ and $X_{17}$ are independently an amino acid having a side chain comprising an acyclic aliphatic moiety;
$X_{16}$ is an amino acid having a side chain comprising a polar moiety or is absent;
$X_{15}$ and $X_{18}$-$X_{20}$ are independently an amino acid having a side chain comprising a polar moiety; and
$X_{21}$ is an amino acid having a side chain comprising an acyclic aliphatic moiety or is absent.

In a fourth embodiment of the first aspect, provided herein is the recombinant peptide of the third embodiment of the first aspect, wherein $X_{14}$, $X_{17}$, and $X_{21}$ are independently selected from the group consisting of alanine, isoleucine, and leucine; and $X_{15}$, $X_{16}$, and $X_{18}$-$X_{20}$ are independently selected from the group consisting of arginine, aspartate, glutamate, glutamine, lysine, and serine.

In a fifth embodiment of the first aspect, provided herein is the recombinant peptide of the first aspect, wherein $X_6$ is phenylalanine, tryptophan, or tyrosine; $X_7$ and $X_8$ are independently selected from the group consisting of threonine, isoleucine, leucine, valine, glutamate, and aspartate; $X_9$ is leucine, isoleucine, valine, or phenylalanine; and $X_{10}$, $X_{11}$, and $X_{12}$ are independently selected from the group consisting of aspartate, glutamate, glutamine, serine, and threonine.

In a sixth embodiment of the first aspect, provided herein is the recombinant peptide of the third embodiment of the first aspect, wherein $X_{14}$, $X_{17}$, and $X_{21}$ are independently selected from the group consisting of alanine, isoleucine, and leucine; and $X_{15}$, $X_{16}$, and $X_{18}$-$X_{20}$ are independently selected from the group consisting of arginine, aspartate, glutamate, glutamine, lysine, and serine.

In a seventh embodiment of the first aspect, provided herein is the recombinant peptide of the first aspect, wherein the recombinant peptide comprises a peptide having at least an 88% sequence homology with SEQ ID NO: 1, SEQ ID NO: 2, SEQ ID NO: 3, SEQ ID NO: 12, SEQ ID NO: 14, SEQ ID NO: 20, or SEQ ID NO: 21.

In an eighth embodiment of the first aspect, provided herein is the recombinant peptide of the first aspect, wherein the recombinant peptide comprises a peptide having SEQ ID NO: 1, SEQ ID NO: 2, SEQ ID NO: 3, SEQ ID NO: 12, SEQ ID NO: 14, SEQ ID NO: 14, SEQ ID NO: 15, SEQ ID NO: 16, SEQ ID NO: 20, or SEQ ID NO: 21.

In a ninth embodiment of the first aspect, provided herein is the recombinant peptide of the seventh embodiment of the first aspect further comprising an affinity tag or detectable label.

In a tenth embodiment of the first aspect, provided herein is the recombinant peptide of the ninth embodiment of the first aspect wherein the detectable label is selected from the group consisting of chromogenic enzymes, radioactive isotopes, chromophores, luminescent compounds, fluorescent compounds, magnetic resonance imaging compounds, superparamagnetic particles, and ultra-small superparamagnetic particles.

In a second aspect, provided herein is a polynucleotide encoding the recombinant peptide of the first aspect.

In a third aspect, provided herein is a method for inhibiting autophagy in a subject for whom inhibition of autophagy is beneficial, comprising administering to the subject a therapeutically effective amount of the recombinant peptide of the first aspect thereby inhibiting autophagy activity in the subject.

In a first embodiment of the third aspect, provided herein is the method of the third aspect, wherein $R_1$ comprises a sequence represented by Formula II:

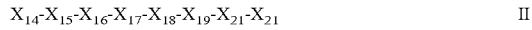   II wherein $X_{14}$ and $X_{17}$ are independently an amino acid having a side chain comprising an acyclic aliphatic moiety;
$X_{16}$ is an amino acid having a side chain comprising a polar moiety or is absent;
$X_{15}$ and $X_{18}$-$X_{20}$ are independently an amino acid having a side chain comprising a polar moiety; and
$X_{21}$ is an amino acid having a side chain comprising an acyclic aliphatic moiety or is absent.

In a second embodiment of the third aspect, provided herein is the method of the third aspect, wherein the recombinant peptide comprises a peptide having at least an 88% sequence homology with SEQ ID NO: 1, SEQ ID NO: 2, or SEQ ID NO: 3, SEQ ID NO: 12, SEQ ID NO: 14, SEQ ID NO: 20, or SEQ ID NO: 21.

In a third embodiment of the third aspect, provided herein is the method of the third aspect, wherein the recombinant peptide comprises a peptide having SEQ ID NO: 1, SEQ ID NO: 2, SEQ ID NO: 3, SEQ ID NO: 12, SEQ ID NO: 14, SEQ ID NO: 14, SEQ ID NO: 15, SEQ ID NO: 16, SEQ ID NO: 20, or SEQ ID NO: 21.

In a fourth aspect, provided herein is a method of inhibiting autophagy in a cell comprising the step of contacting the cell with the recombinant peptide of the first aspect thereby inhibiting autophagy in the cell.

In a first embodiment of the fourth aspect, provided herein is the method of the fourth aspect, wherein R₁ comprises a sequence represented by Formula II:

$$X_{14}\text{-}X_{15}\text{-}X_{16}\text{-}X_{17}\text{-}X_{18}\text{-}X_{19}\text{-}X_{20}\text{-}X_{21} \qquad \text{II}$$

wherein $X_{14}$ and $X_{17}$ are independently an amino acid having a side chain comprising an acyclic aliphatic moiety; $X_{16}$ is an amino acid having a side chain comprising a polar moiety or is absent;
$X_{15}$ and $X_{18}\text{-}X_{20}$ are independently an amino acid having a side chain comprising a polar moiety; and
$X_{21}$ is an amino acid having a side chain comprising an acyclic aliphatic moiety or is absent.

In a second embodiment of the fourth aspect, provided herein is the method of the fourth aspect, wherein the recombinant peptide comprises a peptide having at least an 88% sequence homology with SEQ ID NO: 1, SEQ ID NO: 2, SEQ ID NO: 3, SEQ ID NO: 12, SEQ ID NO: 14, SEQ ID NO: 20, or SEQ ID NO: 21.

In a third embodiment of the fourth aspect, provided herein is the method of the fourth aspect, wherein the recombinant peptide comprises a peptide having SEQ ID NO: 1, SEQ ID NO: 2, SEQ ID NO: 3, SEQ ID NO: 12, SEQ ID NO: 14, SEQ ID NO: 14, SEQ ID NO: 15, SEQ ID NO: 16, SEQ ID NO: 20, or SEQ ID NO: 21.

The recombinant peptides described herein include: AnkG WT from natural rat 480 kD AnkG residues 1985-2010 (PEDDWTEFSSEEIREARQAAASHAPS; SEQ ID NO: 1); AnkG E1991R modified from rat 480 kD AnkG residues 1985-2010 (PEDDWTRFSSEEIREARQAAASHAPS; SEQ ID NO: 2); and AnkB WT from natural human 440 kD AnkB residues 1588-1614 (VEEEWVIVSDEEIEEARQKAPLEITEY, SEQ ID NO: 3); The recombinant peptides can also include modified forms of the recombinant peptides described herein including peptides fitting the aforementioned consensus sequence motif; AnkB and AnkG recombinant peptides derived from AnkB or AnkG from other species (such as mouse, rat, canine, rabbit, rat, zebra fish, etc); and/or those recombinant peptides having 50%, 60%, 70%, 80%, 90%, 93%, 95%, 97%, 98%, 99%, or higher sequence homology with the recombinant peptide sequences described herein. Also contemplated, are peptidomimetics or peptide analogs that are structurally similar to the recombinant peptides described herein, including but not limited to non-proteinogenic (e.g. p-azido-phenylalanine, etc.) or chemically modified (e.g. phosphorylation, acetylation, lipidation etc.) amino acids substitutions, non-peptide linkages, dimeric or oligomeric conjugation, and staple peptides.

The present disclosure also provides dual-role tools for either inhibiting or monitoring autophagy. In one aspect, the Ank-derived peptides can be used as potent inhibitors to block the complexes formed by Atg8s and LIR containing proteins thus inhibiting autophagy as illustrated in cell lines and *C. elegans*. The inhibitory recombinant peptides described herein can be used in the treatment of cancer or other autophagy-related diseases. The recombinant peptides described herein can also be used to screen for autophagy inducers, which are potential drug leads for treating neurodegenerative diseases, such as Alzheimer's disease, Parkinson disease, as well as other autophagy-related diseases. In another aspect, the recombinant peptides described herein can be used as specific markers to monitor the occurrence of autophagy.

DETAILED DESCRIPTION

Figure 1:
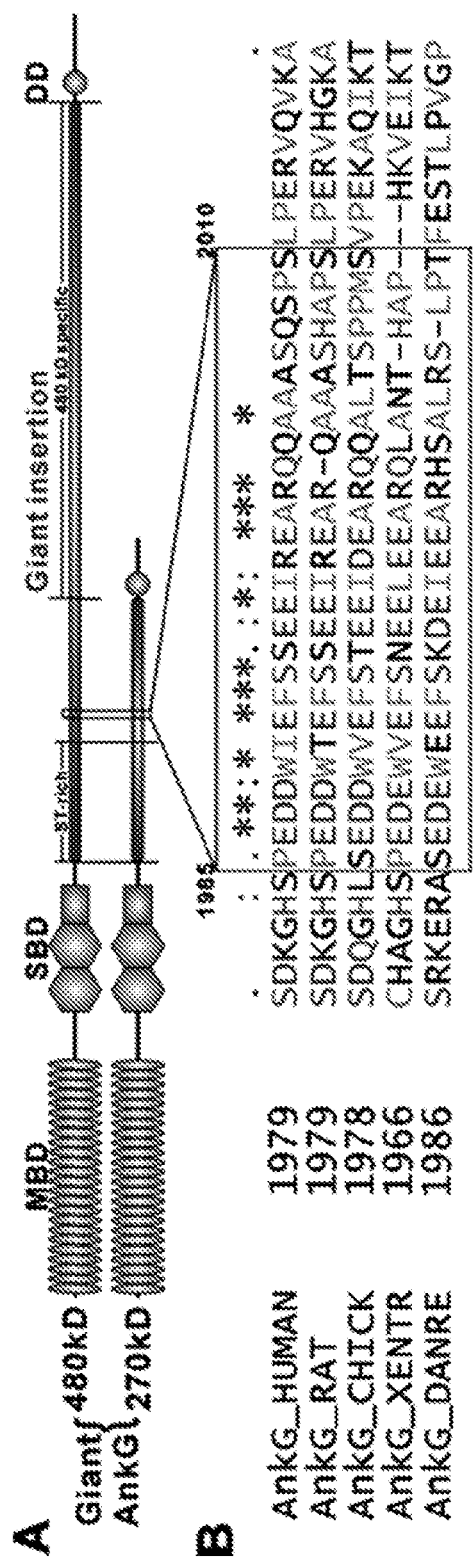
FIG. 1A depicts a diagram showing the domain organization of 270/480 kD AnkG and the location of the LIR sequence in AnkG.
FIG. 1B depicts the sequence alignment of AnkG LIR from vertebrates (SEQ ID NOs:36-40, respectively, in order of appearance).
FIG. 1C depicts isothermal titration calorimetry (ITC) results showing AnkG LIR can bind to GABARAPs with nanomolar range affinities. C1: GABARAP; C2: GABARAPL1; and C3: GABARAPL2.
FIG. 1D depicts the ITC results showing AnkG LIR can bind to LC3s with affinities ranging from hundreds to thousands of nM. D1: LC3A; D2: LC3B; D3: LC3C.
Figure 1:
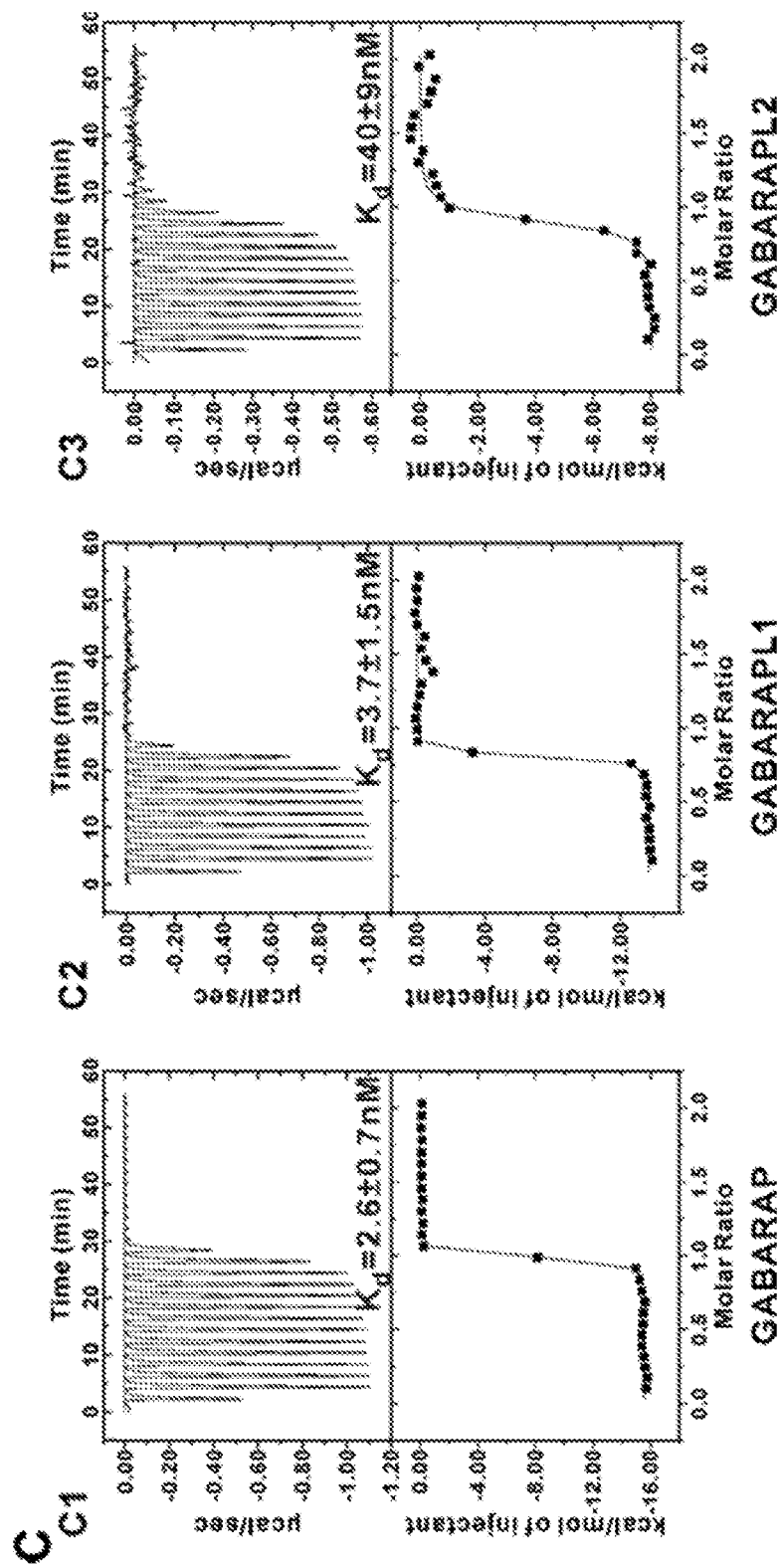
Figure 1:
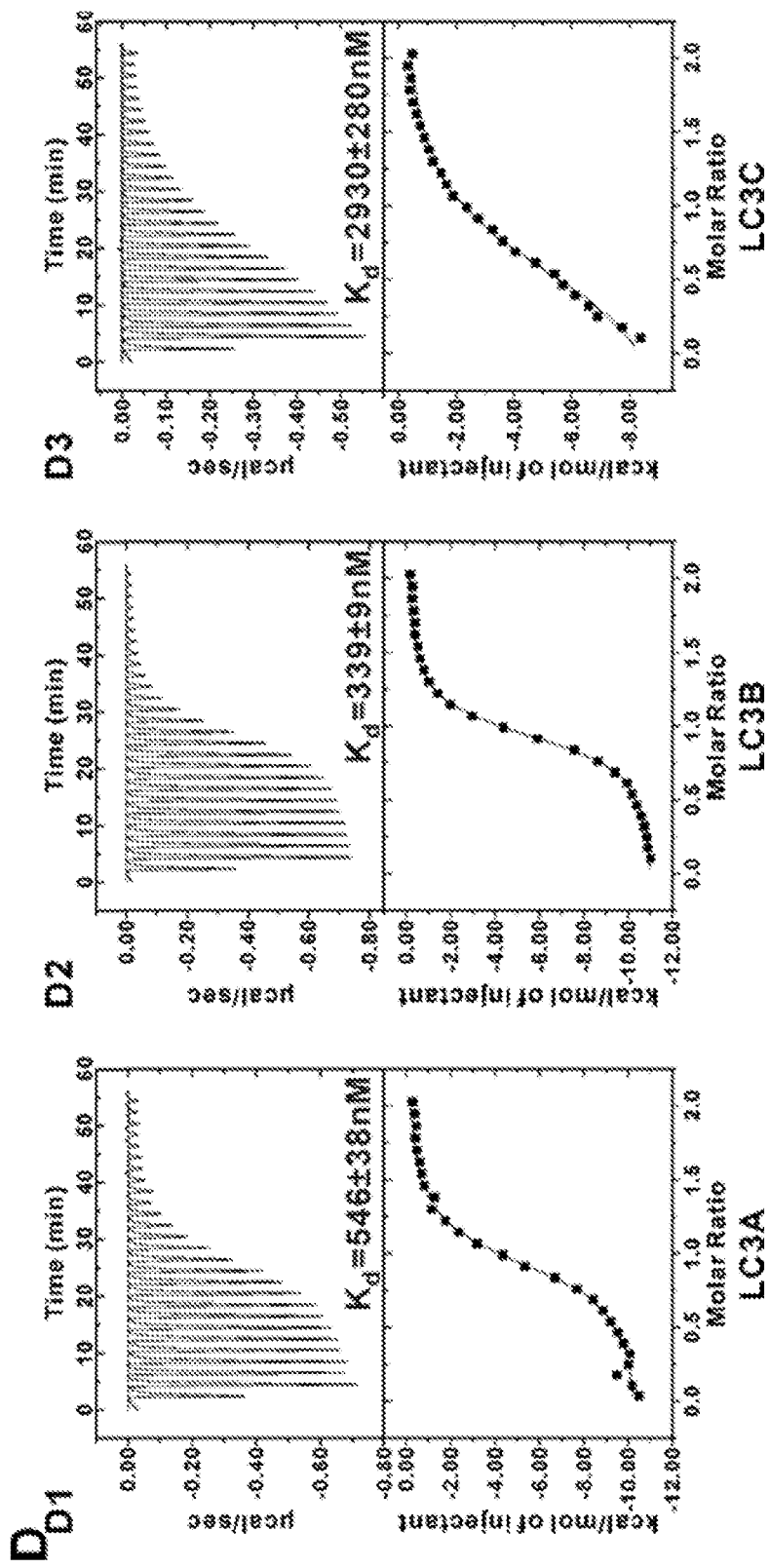

270/480 kD ankyrin-G (AnkG), a neuronal specific isoform of AnkG enriched in axon initial segment and nodes of Ranvier, binds to GABARAP with a $K_d$ ~10-20 nM. The region of AnkG identified for binding to GABARAP contains a LIR motif. The superior affinity of the binding between AnkG and GABARAP prompted an investigation as to whether it might be possible to develop super strong Atg8 binding peptides as autophagy inhibitors based on the LIR motif found in AnkG. This research identified recombinant peptides containing a 23-27 amino acid sequence with surprisingly high affinity to GABARAP and LC3 proteins. By modifying the structure of the recombinant peptides, recombinant peptides with improved selectivity against GABARAP or LC3 can be prepared.

Definitions

The definitions of terms used herein are meant to incorporate the present state-of-the-art definitions recognized for each term in the field of biotechnology. Where appropriate, exemplification is provided. The definitions apply to the terms as they are used throughout this specification, unless otherwise limited in specific instances, either individually or as part of a larger group.

The term "attach" or "attached" as used herein, refers to connecting or uniting by a bond or non-bonding interaction in order to keep two or more compounds together, which encompasses either direct or indirect attachment such that for example where a first polypeptide is directly bound to a second polypeptide or other molecule, and the embodiments wherein one or more intermediate compounds (e.g., a linker), such as a polypeptide, is disposed between the first polypeptide and the second polypeptide or other molecule.

The term "protein", "polypeptide", or "peptide" as used herein indicates an organic polymer composed of two or more amino acid monomers and/or analogs thereof. The term "polypeptide" or "peptide" includes amino acid polymers of any length including full length proteins and peptides, as well as analogs and fragments thereof. A polypeptide of three or more amino acids is also called an oligopeptide. As used herein, the term "amino acid", "amino acidic monomer", or "amino acid residue" refers to any of the twenty naturally occurring amino acids including synthetic amino acids with unnatural side chains and including both D and L optical isomers. The term "amino acid analog" refers to an amino acid in which one or more individual atoms have been replaced, either with a different atom, isotope, or with a different functional group but is otherwise identical to its natural amino acid analog.

The term "amino acid" refers to naturally occurring and non-natural amino acids, as well as amino acid analogs and amino acid mimetics that function in a manner similar to the naturally occurring amino acids. Naturally encoded amino acids are the 20 common amino acids (alanine, arginine, asparagine, aspartate, cysteine, glutamine, glutamate, glycine, histidine, isoleucine, leucine, lysine, methionine, phenylalanine, proline, serine, threonine, tryptophan, tyrosine, and valine) and pyrrolysine and selenocysteine. Amino acid analogs refers to compounds that have the same basic chemical structure as a naturally occurring amino acid, i.e., an α carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid.

As used herein, the term "unnatural amino acid" or the like refers to any amino acid, modified amino acid, and/or amino acid analogue that is not one of the 20 common naturally occurring amino acids, selenocysteine or pyrrolysine.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

As used herein, the term "variant" refers to a polynucleotide or nucleic acid differing from a reference nucleic acid or polypeptide, but retaining essential properties thereof. Generally, variants are overall closely similar, and, in many regions, identical to the reference nucleic acid or polypeptide.

A variant can, for example, comprise the amino acid sequence of the parent polypeptide sequence with at least one conservative amino acid substitution. Alternatively or additionally, the variant can comprise the amino acid sequence of the parent polypeptide sequence with at least one non-conservative amino acid substitution. In this case, it is preferable for the non-conservative amino acid substitution to not interfere with or inhibit the biological activity of the functional variant. The non-conservative amino acid substitution may enhance the biological activity of the variant, such that the biological activity of the variant is increased as compared to the parent polypeptide.

Amino acid substitutions of the described polypeptides can be conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Cys, Val, etc.), a basic/positively charged polar amino acid substituted for another basic/positively charged polar amino acid (e.g. Lys, His, Arg, etc.), an uncharged amino acid with a polar side chain substituted for another uncharged amino acid with a polar side chain (e.g., Asn, Gln, Ser, Thr, Tyr, etc.), an amino acid with a beta-branched side-chain substituted for another amino acid with a beta-branched side-chain (e.g., Ile, Thr, and Val), an amino acid with an aromatic side-chain substituted for another amino acid with an aromatic side chain (e.g., His, Phe, Trp, and Tyr), etc.

The terms "percentage homology" and "percentage sequence identity", when used in reference to a polypeptide or polynucleotide sequence, are used interchangeably herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Homology is evaluated using any of the variety of sequence comparison algorithms and programs known in the art. Such algorithms and programs include, but are by no means limited to, TBLASTN, BLASTP, FASTA, TFASTA, and CLUSTALW [Pearson and Lipman, 1988, Proc. Natl. Acad. Sci. USA 85(8):2444-2448; Altschul et al., 1990, J. Mol. Biol. 215(3):403-410; Thompson et al., 1994, Nucleic Acids Res. 22(2):4673-4680; Higgins et al. 1996, Methods Enzymol. 266:383-402; Altschul et al., 1990, J. Mol. Biol. 215(3):403-410; Altschul et al., 1993, Nature Genetics 3:266-272]. In certain embodiments, protein and nucleic acid sequence homologies are evaluated using the Basic Local Alignment Search Tool ("BLAST") which is well known in the art (see, e.g., Karlin and Altschul, 1990, Proc. Natl. Acad. Sci. USA 87:2267-2268; Altschul et al., 1990, J. Mol. Biol. 215:403-410; Altschul et al., 1993, Nature Genetics 3:266-272; Altschul et al., 1997, Nuc. Acids Res. 25:3389-3402).

As used herein, the terms "treat", "treating", "treatment", and the like refer to reducing or ameliorating a disorder/disease and/or symptoms associated therewith. It will be appreciated, although not precluded, treating a disorder or condition does not require that the disorder, condition, or symptoms associated therewith be completely eliminated. In certain embodiments, treatment includes prevention of a disorder or condition, and/or symptoms associated therewith. The term "prevention" or "prevent" as used herein refers to any action that inhibits or at least delays the development of a disorder, condition, or symptoms associated therewith. Prevention can include primary, secondary and tertiary prevention levels, wherein: a) primary prevention avoids the development of a disease; b) secondary prevention activities are aimed at early disease treatment, thereby increasing opportunities for interventions to prevent progression of the disease and emergence of symptoms; and c) tertiary prevention reduces the negative impact of an already established disease by restoring function and reducing disease-related complications.

As used herein, the term "subject" refers to any animal (e.g., a mammal), including, but not limited to, humans, non-human primates, canines, felines, bovines, and rodents.

The phrase "consisting essentially of is herein meant to define the scope of the recombinant peptides to the specified material amino acids, and to only include additional amino acids or changes that do not materially affect the claimed invention's basic and novel characteristics, namely, e.g., the binding affinity of the recombinant peptides to Atg8 protein family members.

As used herein, the term "recombinant protein", "recombinant peptide", or the like refers to any protein of interest that can be manufactured using recombinant DNA technology.

Recombinant host cells may be any of the host cells used for recombinant protein production, including, but not limited to, bacteria, yeast, insect and mammalian cell lines.

Recombinant host cells may be made by transforming host cells with expression vectors containing DNA coding for the recombinant peptide of interest.

The recombinant peptides comprising the Formula I and other sequences provided herein specifically exclude naturally occurring proteins that include the sequences described herein (e.g., naturally occurring full length AnkB, AnkG, and FAM134B). In certain embodiments, the recombinant peptides described herein exclude peptides sequences that comprise the recombinant peptide of Formula I and other sequences provided herein and are equal to or longer than 35, 30, 35, 40, 45, or 50 amino acids of any naturally occurring AnkB, AnkG, and FAM134B protein. In certain embodiments, the recombinant peptides described herein exclude peptides sequences that comprise the recombinant peptide of Formula I having more than 5, 10, 15, or 20 flanking amino acids at the n-terminus and/or the c-terminus of the recombinant peptide of Formula I that are naturally flanking amino acids at the equivalent extended LIR peptide sequence in naturally occurring AnkB, AnkG, and FAM134B proteins.

The AnkG LIR motif is located at the N-terminal part of the giant insertion shared by the two giant AnkG isoforms (270/480 kD AnkG) (FIG. 1A). Via measuring quantitative binding constants between GABARAP and various truncated AnkG fragments, the minimal GABARAP binding region of AnkG to an about 26-aa containing peptide (aa 1985-2010, also referred to as AnkG LIR (SEQ ID NO: 1) herein) was mapped, which is somewhat longer than known LIR sequences (FIG. 1B). Surprisingly, the identified polypeptide sequence is evolutionarily conserved in AnkG and binds to GABARAP with $K_d$ ~2.6 nM measured by the isothermal titration calorimetry (ITC) assay (FIG. 1B & C1). It is noted that the binding between the AnkG LIR (SEQ ID NO:1) and GABARAP is ~1000-fold stronger than almost all reported bindings between LIR motifs and Atg8s, qualifying AnkG LIR as a super strong GABARAP binder. AnkG LIR (SEQ ID NO:1) can also bind to GABARAPL1 with a super strong affinity ($K_d$ ~3.7 nM) and to GABARAPL2 (also known as GATE-16) with a somewhat lower affinity ($K_d$ ~40 nM, FIG. 1C2 & 1C3). Surprisingly, the ITC results showed that AnkG LIR binds to the LC3s with $K_d$ values ranging from hundreds to thousands of nM, which are comparable to the bindings between canonical LIRs and LC3s (FIG. 1D), indicating that AnkG LIR can differentiate between the two subfamilies of Atg8s and can selectively bind to the GABARAPs.

In order to elucidate the molecular basis governing the super strong and selective binding between AnkG LIR and GABARAPs, we determined the crystal structures of AnkG LIR in complex with GABARAPL1 and with LC3B, respectively. The crystals of the AnkG LIR/GABARAPL1 complex were diffracted to 1.85 Å resolution and the structure was solved by the molecular replacement methods. In the complex, 23 (Pro1985-His2007) out of the total 26 residues of AnkG LIR can be clearly traced in the electron density map. The GABARAPL1-bound AnkG LIR is composed of two parts: the N-terminal extended structure formed by the LIR core containing the signature "ΦXXΨ"-motif and a C-terminal extension containing a three-turn α-helix (termed as "C-helix", covering Glu1996 to Ala2003), which is missing in most of the reported LIRs (FIG. 2A). The two aromatic residues Trp1989 and Phe1992 in the LIR core insert deep into the two hydrophobic pockets, and this binding is essentially the same as those between reported LIRs and all Atg8s (FIG. 2B). As expected, substitution of Trp1989 with Arg led to a dramatic weakening of the binding of AnkG LIR to GABARAP and to LC3 (FIG. 2E). The C-helix is nearly perpendicular to α3 of GABARAPL1 and extensively interacts with a number of residues from α3 and α4 of GABARAPL1 (FIG. 2C). Removal of half of the C-helix (i.e. truncating aa 2001-2010) from AnkG LIR resulted in a ~200-fold decrease of its binding to GABARAP (the construct "1985-2000" in FIG. 2E), indicating that the C-helix is required for the super strong binding. However, the AnkG LIR C-helix alone (aa 1993-2010) has no detectable binding to GABARAP (FIG. 2E). Therefore, we conclude that the synergistic actions of the canonical LIR-motif and the extended C-helix render AnkG LIR with super strong binding to GABARAP and the unique C-helix presumably provides binding specificity between AnkG LIR and GABARAPs. The binding interface between the C-helix and GABARAPL1 α3/α4, which has not been observed in other LIR/Atg8 interactions, can be divided into three layers. The upper layer involves two salt bridges (Glu1996-Arg67 and Glu1999-Lys66); the middle layer is mediated by hydrophobic interactions between Ile1997/Ala2000/Ala2003 and Leu63/Phe62; and the lower layer is composed of Arg2001 forming a salt bridge with Asp54 and hydrogen bond with Gln59 (FIG. 2C). It is noted that a number of reported LIRs often end with a Glu residue corresponding to Glu1996 in AnkG LIR, and this Glu also forms a salt bridge with Arg67 in GABARAPL1 (or the corresponding Arg in other Atg8 members) (Cheng et al., 2016; Olsvik et al., 2015). Charge reversal mutations of Glu1996 or Arg67 or substitution of the hydrophobic Ile1997 or Ala2000 with Gln invariably decreased the binding between AnkG LIR and GABARAP (FIG. 2E).

The structure of AnkG LIR/LC3B complex was determined at the 2.6 Å resolution. The overall structure and the binding mode of the AnkG LIR/LC3B complex are generally similar to that of AnkG LIR/GABARAPL1 (RMSD of 0.86 Å; FIG. 2D) with an important difference that the LC3-bound AnkG LIR C-helix is significantly shorter, covering only Glu1996-Arg2001 instead of Glu1996-His2007 in the GABARAPL1 complex. This structural finding explains why AnkG LIR binds to LC3s with much weaker affinity than to GABARAPs (FIG. 1). The shorter C-helix of AnkG LIR is nevertheless also engaged in and important for LC3 binding, as substitutions of the critical residues or truncating the C-helix decreased or even completely abolished AnkG LIR's binding to LC3 (FIG. 2E). Interestingly, we observed that Glu1991 interacts with Lys29 and His27 of LC3B whereas the same Glu only weakly interacts with Arg28 of GABARAPL1 (corresponding to Lys29 of LC3B). We predicted that substitution of Glu1991 with Arg would weaken AnkG LIR's binding to LC3s but have limited impact on its binding to GABARAPs, so that the mutant AnkG LIR might have even higher selectivity in binding to GABARAPs over LC3s. Indeed, the Glu1991Arg AnkG LIR binds to GABARAP with a slightly weaker affinity but to LC3A with a ~10-fold lower affinity, thereby increasing the selectivity between GABARAP and LC3A to ~1000-fold (FIG. 2E).

The super strong binding of AnkG LIR to GABARAP prompted us to search for possible existence of other naturally occurring, strong Atg8 binding proteins. A BLAST search using AnkG LIR as the template against the human proteome returned a similar extended LIR sequence from the 440 kD giant AnkB as the top candidate, and we refer it as AnkB LIR (SEQ ID NO:3) (FIGS. 3A & B). The 440 kD AnkB and 480 kD AnkG both contain a giant exon encoding several thousand amino acid residues, though the homology between the two giant exon coding sequences is very limited. The 440 kD AnkB is also a neuronal specific isoform, and is mainly expressed in unmyelinated/premyelinated axons. AnkB LIR (SEQ ID NO:3) also contains a LIR core "ΦXXΨ" followed by a stretch of amino acid residues with rather limited homology with the AnkG LIR C-helix (FIG. 3B). Nevertheless, the sequence of AnkB LIR is highly conserved in the 440 kD AnkB throughout the evolution (FIG. 3B). We found with a pleasant surprise that AnkB LIR (SEQ ID NO:3) binds to GABARAP with an affinity about 10-fold higher than AnkG LIR (SEQ ID NO: 1) does ($K_d$ values of ~0.27 nM vs 2.6 nM; FIG. 3C vs FIG. 1C). Even more surprisingly, AnkB LIR binds to all members of the Atg8 family with super strong affinities with $K_d$ values ranging from the strongest of ~0.21 nM to the weakest of ~10.5 nM (FIGS. 3C&D).

Figure 2:
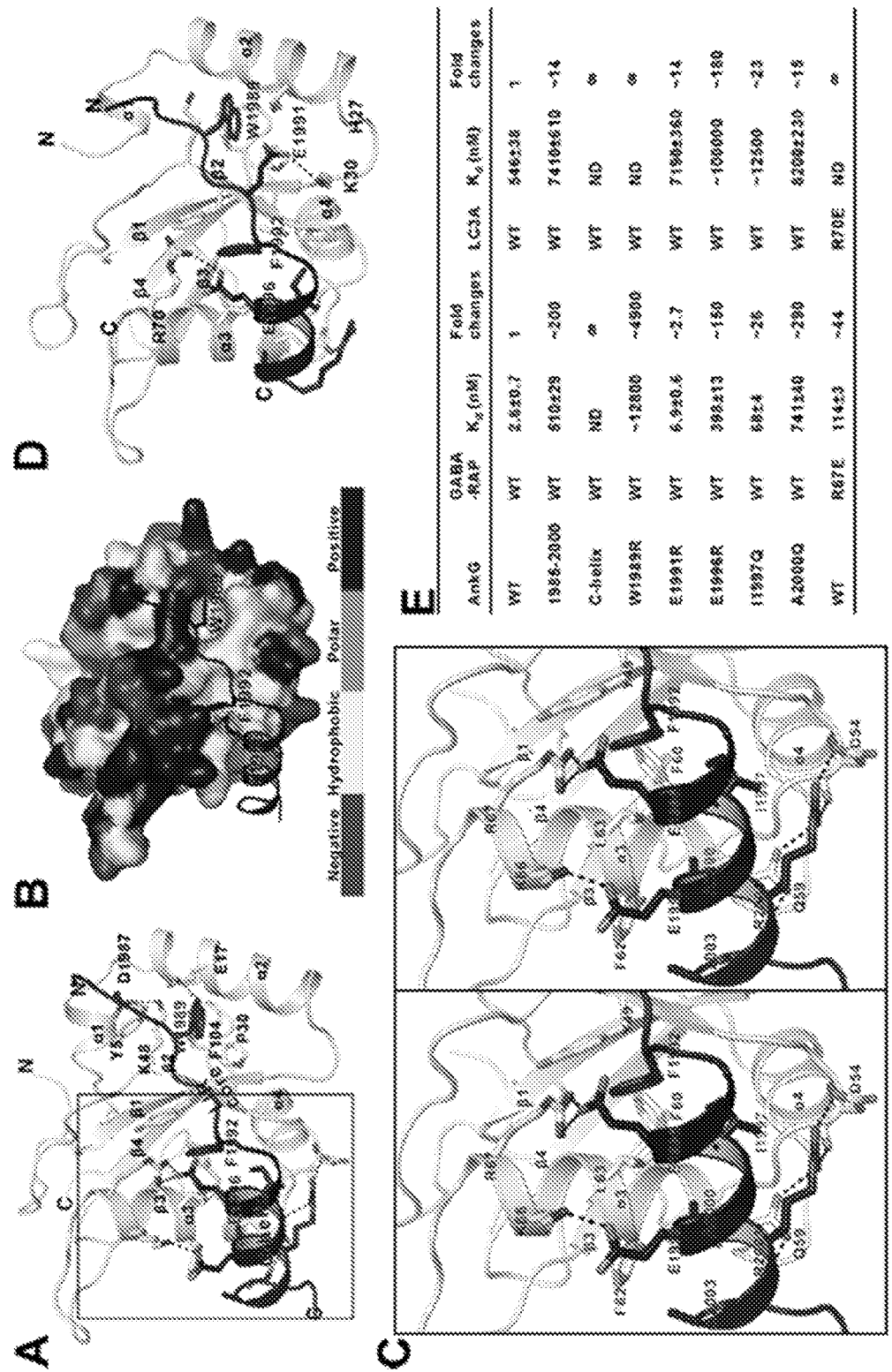
FIG. 2A depicts a ribbon representation of the AnkG LIR/GABARAPL1 complex structure. Key residues critical for the binding are shown in the stick model. Salt bridges and hydrogen bonds are indicated with dashed lines.
FIG. 2B depicts the combined surface (GABARAPL1) and ribbon-stick model (AnkG LIR) showing the two hydrophobic pockets of GABARAPL1 accommodating the LIR core and the C-helix of AnkG.
FIG. 2C depicts a stereo view showing the detailed interactions of the AnkG LIR C-helix and GABARAPL1.
FIG. 2D depicts a ribbon representation of the AnkG LIR/LC3B complex structure. Key residues critical for binding are shown in the stick model.
FIG. 2E is a table summarizing the dissociation constants derived from ITC experiments showing that truncations or mutations of the critical residues in the interface either weaken or even abolish bindings to GABARAP and/or LC3A.
Figure 3:
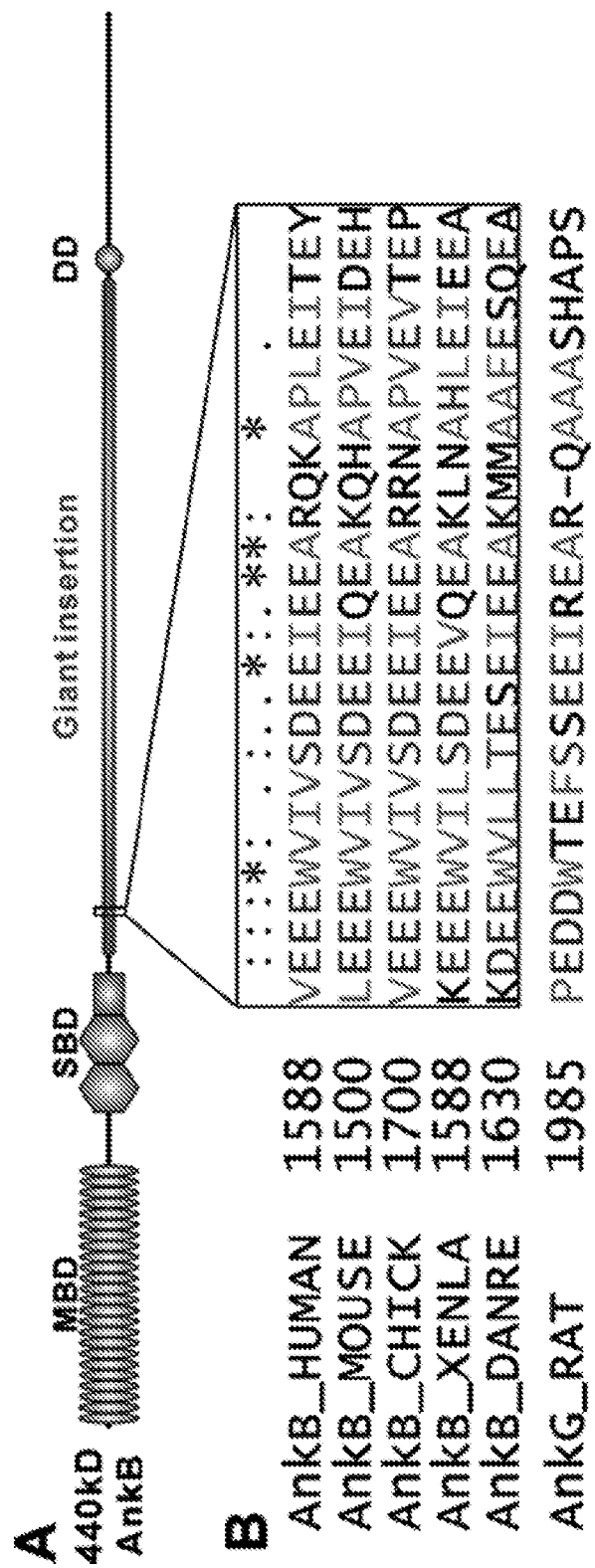
FIG. 3A depicts a diagram showing the domain organizations of 440 kD AnkB and the locations of the extended LIR sequence only in the giant AnkB.
FIG. 3B depicts the sequence alignment of AnkB LIR (SEQ ID NOs: 3, 8, 9, 41, and 10, respectively, in order of appearance) in vertebrates. AnkG LIR (SEQ ID NO: 1) is also included as a reference.
FIG. 3C depicts ITC results showing the AnkB LIR (SEQ ID NO: 3) recombinant peptide binding to GABARAPs. Note that $K_d$ values for AnkB LIR (SEQ ID NO: 3) and GABARAPs were derived from competition-based ITC experiments due to their super strong bindings.
FIG. 3D depicts ITC results showing the binding of the AnkB LIR (SEQ ID NO: 3) recombinant peptide to LC3s.
Figure 3:
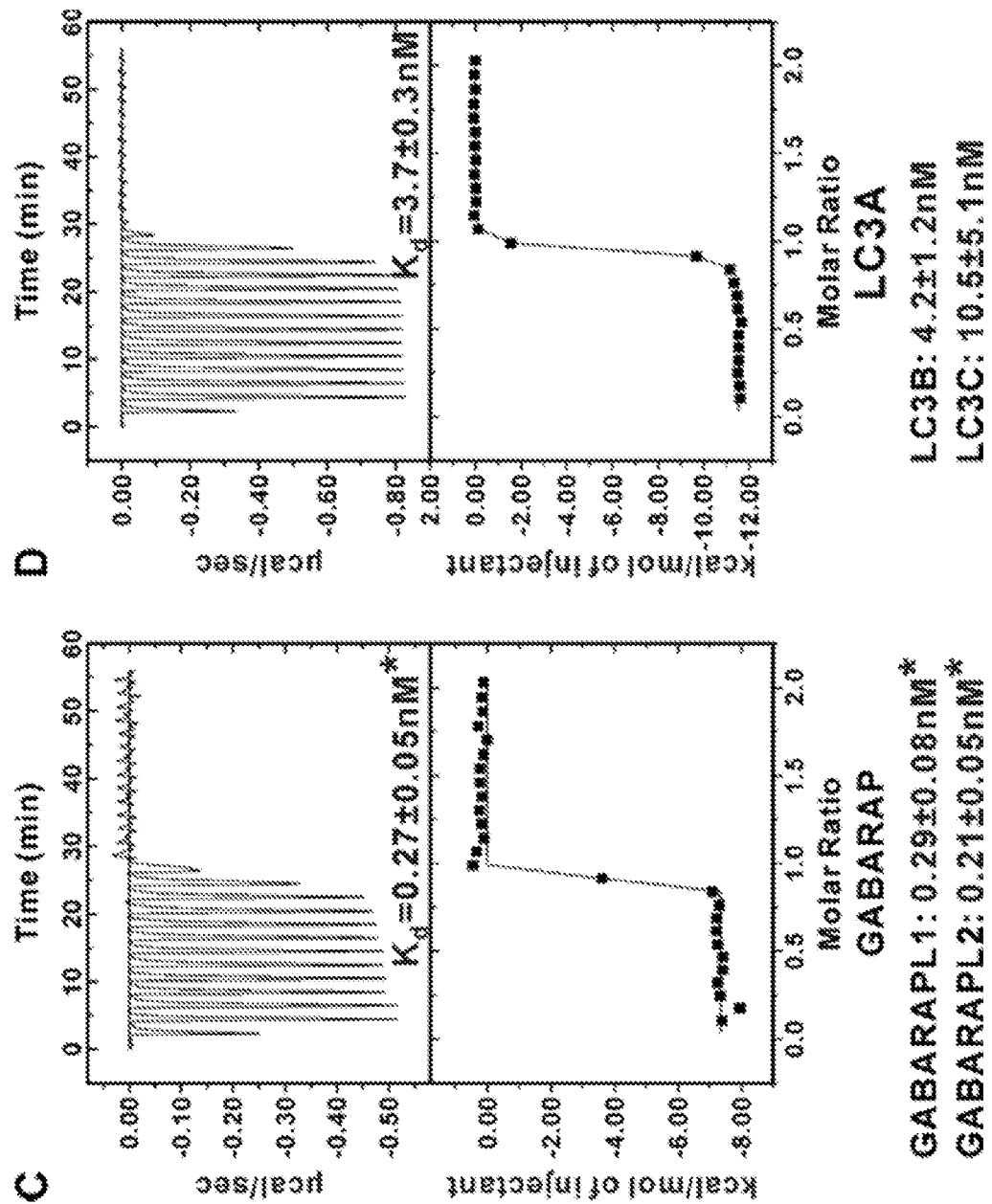
Figure 4:
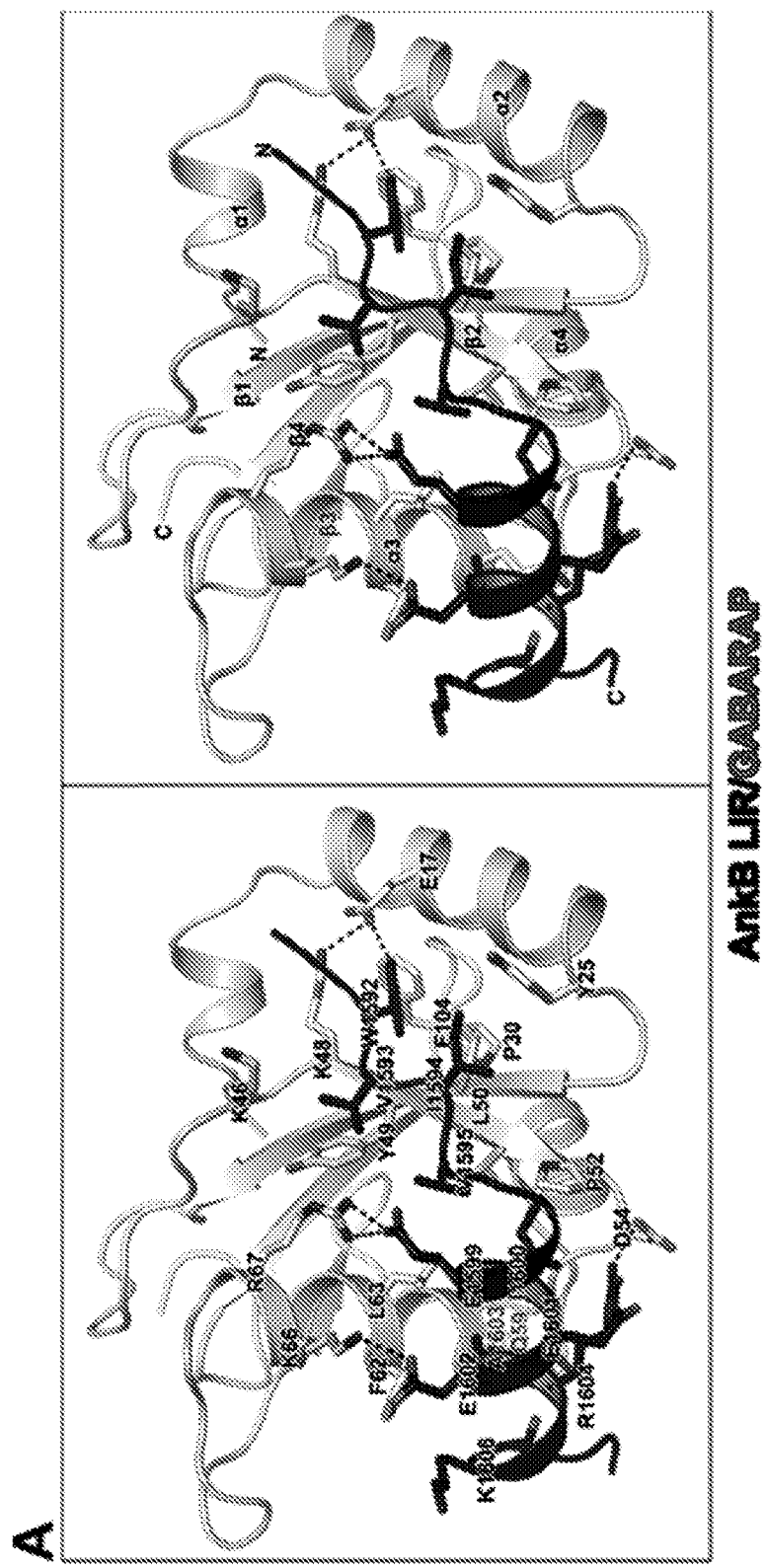
FIG. 4A depicts the stereo view of AnkB LIR (SEQ ID NO: 3) in complex with GABARAP. Residues critical for the binding are highlighted with stick model. Salt bridges and hydrogen bonds are indicated with dashed lines.
FIG. 4B depicts the stereo view of AnkB LIR (SEQ ID NO: 3) in complex LC3B. Residues critical for the binding are highlighted with stick model. Salt bridges and hydrogen bonds are indicated with dashed lines.
FIG. 4C summarizes the dissociation constants derived from ITC showing that mutations of the critical residues in the interface weakened the bindings.
Figure 4:
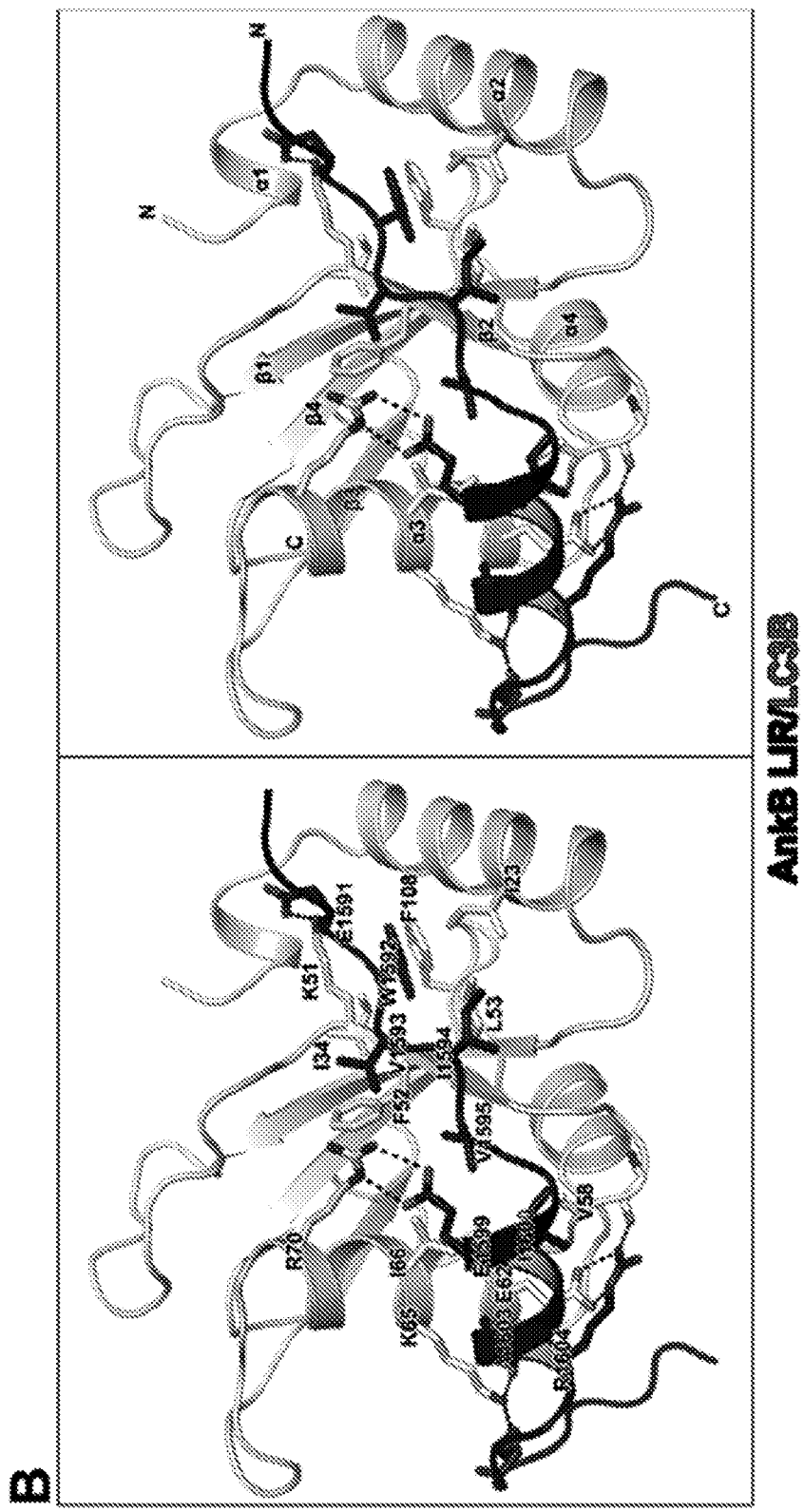

To understand the mechanisms governing the strong interactions between AnkB LIR (SEQ ID NO:3) and Atg8s, we solved the crystal structures of the AnkB LIR/GABARAP and AnkB LIR/LC3B complexes at 2.75 Å and 2.2 Å resolutions, respectively (FIGS. 4A&B). The overall structural features of the bindings of AnkB LIR (SEQ ID NO:3) to GABARAP and LC3B are highly similar to those of the bindings of AnkG to GABARAPL1 and LC3B (FIGS. 2&4). Thus, we will not describe the overall structures of the two complexes any further, except to note that the AnkB LIR also contains a well-defined C-helix extension following the LIR core motif. As expected again, substitution of Trp1592 (the first hydrophobic residue in the canonical "ΦXXΨ" LIR-motif) by Arg dramatically decreased the bindings of AnkB LIR to all members of the human Atg8 family (FIG. 4C). Thus, this Trp1592Arg mutant of AnkB LIR serves as a wonderful control for our functional studies of autophagy inhibition both in cell cultures and in vivo settings below.

There are several subtle but significant differences when comparing the bindings of AnkB LIR (SEQ ID NO:3) and AnkG LIR (SEQ ID NO:1) to the Atg8 members, which can explain why AnkB LIR binds to Atg8s uniformly stronger than AnkG LIR does. The two middle residues in the "ΦXXΨ" LIR-motif of AnkB LIR are also hydrophobic (Val1593 and Ile1594, corresponding to Thr1990 and Glu1991 in AnkG LIR; FIG. 3B), and these two residues actively interact with a number of hydrophobic residues either from GABARAP or LC3B (FIG. 4). In AnkG LIR, only Glu1991 strongly engages in binding to LC3B (FIGS. 2A&D). In the AnkB LIR/LC3B complex, the side chain of Lys65 from LC3B forms hydrogen bonds with the backbone of two residues from the AnkB LIR C-helix (FIG. 4), providing an explanation to why Lys65 in the LC3 subfamily can favorably interact with AnkB LIR but not with AnkG LIR.

Figure 5:
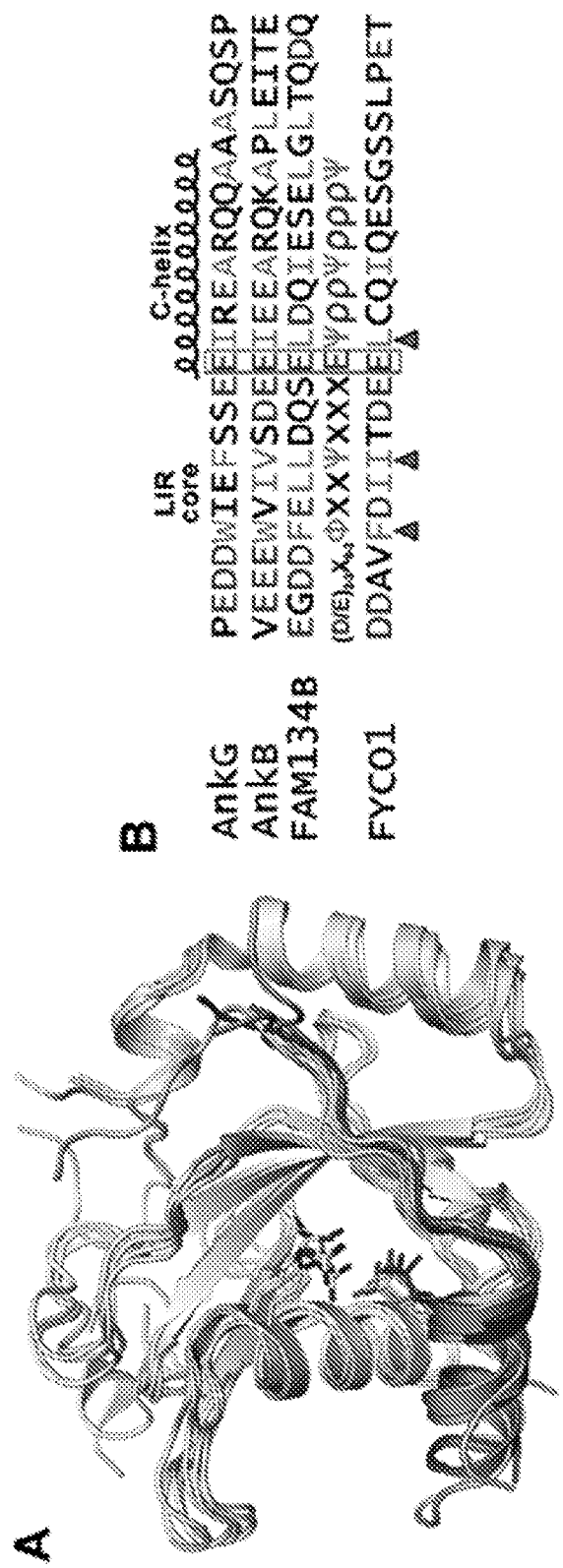
FIG. 5A depicts the superposition of the AnkG/GABARAPL1, AnkG/LC3B, AnkB/GABARAP, AnkB/LC3B and FYCO1/LC3A (PDB: 5CX3) complex structures showing the common binding mode of Atg8s to the extended LIR sequences: the LIR core followed by the C-helix starting with Glu.
FIG. 5B shows the sequence alignment of LIRs (SEQ ID NOs:42-43, 21, and 20) containing a LIR core together with an amphiphilic C-helix. The consensus sequence "(D/E)$_{2\text{-}3}$X$_{0\text{-}2}$ΦXXΨXXXEΨρρΨρρρΨ" is also shown, where Φ represents aromatic residues; Ψ represents aliphatic residues; ρ represents polar residues; and X represents any residues.
FIG. 5C depicts ITC results showing that GABARAP binds to FAM134B LIR (SEQ ID NO. 21) with C-helix extension much stronger than that without the C-helix.
FIG. 5D depicts ITC results showing that charge reverse mutations of the predicted E462/R67 salt bridge weaken or even disrupt the binding between FAM134B (SEQ ID NO. 21) and GABARAP.
Figure 5:
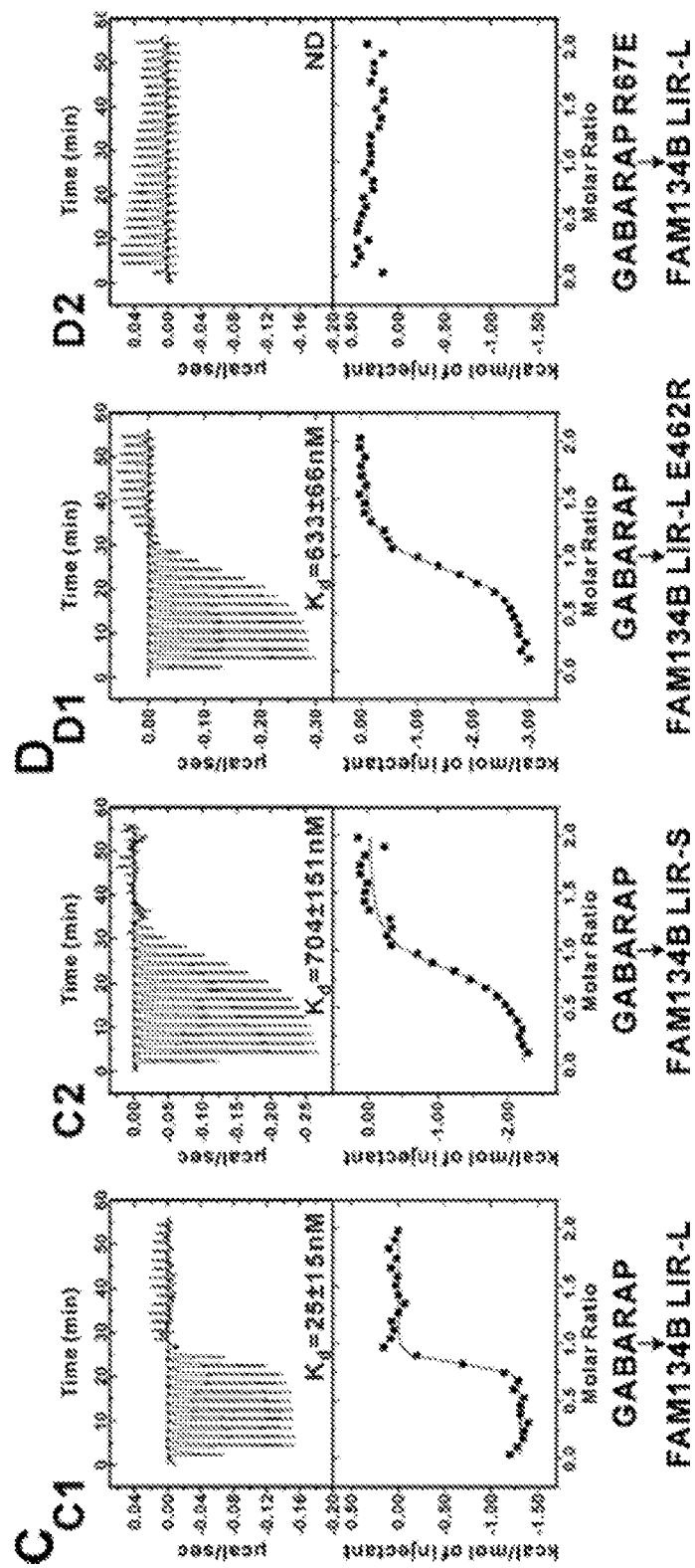

A defining feature for the strong Atg8 binding sequences from AnkB and AnkG LIR revealed from the above structural studies is the presence of a ~10-residue amphipathic α-helix (the C-helix) immediately following the canonical LIR-motif (FIG. 5B). A Glu residue at the beginning of the C-helix forms a pair of salt bridges with an absolutely conserved Arg (Arg67 in GABARAP and Arg70 in LC3A) at the end of α3 in all Atg8s (FIG. 5A and FIG. 4). Three non-aromatic hydrophobic residues at the positions 1-4-8 immediately following this Glu residue are aligned on the same face of the C-helix and interact with the hydrophobic surface formed by α3 of Atg8s. Due to the non-specific nature of the hydrophobic interactions, the three hydrophobic residues are rather degenerate as long as they are not so bulky since the hydrophobic surface of Atg8 is relatively flat (FIG. 2B). We searched the human proteome for possible existence of other super strong Atg8 binders using the following two criteria: existence of a canonical LIR-motif immediately followed by a three-turn or longer amphipathic α-helix starting with a Glu residue. Such search returned with several potential candidates. Among these, FAM134A/B/C (also known as Reticulophagy regulator 2/1/3, respectively) fits particularly well with the searching criteria (FIG. 5B). FAM134B and its yeast orthologue Atg40 have been implicated to involve in selective autophagy to facilitate degradation of endoplasmic reticulum (called ER-phagy) by binding to Atg8s (Khaminets et al., 2015; Mochida et al., 2015). We tested the binding of GABARAP to human FAM134B LIR (SEQ ID NO: 21) with or without the C-helix extension (referred to as "LIR-L" for aa 448-469 and "LIR-S" for aa 448-461; Glu462 is predicted to be the beginning residue of the C-helix, equivalent to Glu1996 in AnkG LIR) using ITC-based assay. In agreement with our prediction, GABARAP binds to FAM134B LIR-L with a very high affinity ($K_d$ ~25 nM; FIG. 5C). Truncation of the predicted C-helix led to a dramatic decrease of its binding to GABARAP ($K_d$ dropped to 704 nM; FIG. 5C). Additionally, the charge reversal mutations of Glu462 in FAM134B or Arg67 in GABARAP led to decrease or even total disruption of the binding (FIG. 5D), suggesting that FAM134B adopts a similar binding mode as AnkB/G LIRs do. Taken all above data together, we derive a consensus sequence motif for the extended LIRs with super strong Atg8 binding affinities: "(D/E)$_{2-3}$X$_{0-2}$ΦXXΨXXXEΨρρΨρρρΨ", where Φ represents aromatic residues; Ψ represents aliphatic residues; ρ represents polar residues; and X represents any residues (FIG. 5B).

We noted that a recently identified LC3 binding sequence from FYCO1 (SEQ ID NO: 20) has a sequence feature partially fitting the super strong Atg8 binding motif by having a one-turn helix extension following the canonical LIR-motif and with a Glu followed by a Leu at the beginning of the helix (Cheng et al., 2016; Olsvik et al., 2015) (FIGS. 5A&B). The C-helix of FYCO1 LIR is shorter than the AnkB/G LIRs. Accordingly, the binding between FYCO1 LIR to LC3 is significantly weaker than the bindings of AnkB LIR to Atg8.

The consensus sequence motif for the extended LIRs with super strong Atg8 binding affinities: "(D/E)$_{2-3}$X$_{0-2}$ΦXXΨXXXEΨρρΨρρρΨ" can also be represented by a recombinant peptide comprising a sequence represented by Formula I:

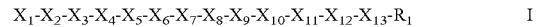

$$X_1\text{-}X_2\text{-}X_3\text{-}X_4\text{-}X_5\text{-}X_6\text{-}X_7\text{-}X_8\text{-}X_9\text{-}X_{10}\text{-}X_{11}\text{-}X_{12}\text{-}X_{13}\text{-}R_1 \qquad I$$

or a pharmaceutically acceptable salt or zwitterion thereof, wherein $X_1$, $X_2$, and $X_3$, are independently aspartate, glutamate, or absent; $X_4$ and $X_5$ are independently any amino acid or absent; $X_6$ is an amino acid having a side chain comprising an aromatic or heteroaromatic moiety; $X_7$ and $X_8$ are independently any amino acid; $X_9$ is an amino acid having a side chain comprising an acyclic aliphatic or an aromatic moiety; $X_{10}$, $X_{11}$, and $X_{12}$ are independently any amino acid; $X_{13}$ is glutamate or arginine; and $R_1$ is an amphipathic alpha helix comprising between 7 and 15 amino acids, wherein at least two of $X_1$, $X_2$, and $X_3$, are selected from aspartate and glutamate.

The recombinant peptides described herein can generally have high binding affinity to both GABARAP and LC3 protein families and as such can be used as inhibitors of the function of both protein families. However, the selectivity of the recombinant peptides described herein between GABARAP and LC3 can be modified by the appropriate structural modification of the recombinant peptides described herein to afford recombinant peptides that are capable of binding to more selectively to one of GABARAP or LC3 over the other. Such selective recombinant peptides can be useful as biochemical probes for studying the function GABARAP or LC3. For example, as demonstrated in FIGS. 2E and 4C, E1599R modification of AnkB (SEQ ID NO: 12); E1996R modification of AnkG (SEQ ID NO: 14); and E1991R modification of AnkG (SEQ ID NO: 2) all result an increase in selectivity towards GABARAP proteins.

In certain embodiments, when $X_{13}$ is arginine, the recombinant peptide must comprise a peptide having at least an 84% sequence homology with SEQ ID NO: 12 or SEQ ID NO: 14. In certain embodiments, $X_{13}$ is arginine and the recombinant peptide comprises a peptide having at least 88%, at least 92%, at least 96% or 100% sequence homology with SEQ ID NO: 12. In certain embodiments, $X_{13}$ is arginine and the recombinant peptide comprises a peptide having at least 88%, at least 92%, at least 96% or 100% sequence homology with SEQ ID NO: 14.

In certain embodiments, $X_{13}$ is glutamate.

Amino acids having a side chain comprising an aliphatic moiety include glycine, alanine, leucine, isoleucine, valine, and proline.

Amino acids having a side chain comprising an acyclic aliphatic moiety include glycine, alanine, leucine, isoleucine, and valine.

Amino acids having a side chain comprising an aromatic moiety include phenylalanine and tyrosine.

Amino acids having a side chain comprising a heteroaromatic moiety include tryptophan and histidine.

Amino acids having a side chain comprising a polar moiety can include both uncharged amino acids, such as serine, threonine, cysteine, asparagine, glutamine, and tyrosine; and charged amino acids, such as arginine, glutamate, aspartate, lysine, and histidine.

Amino acids having a side chain comprising a carboxylic moiety can include aspartate and glutamate.

Amino acids having a side chain comprising an amide moiety can include asparagine and glutamine.

In certain embodiments, $X_1$, $X_2$, and $X_3$ are independently selected from aspartate and glutamate and $X_4$ and $X_5$ are absent. In certain embodiments, $X_1$, $X_2$, and $X_3$ are independently selected from aspartate and glutamate; $X_4$ and $X_5$ are absent; and $X_{13}$ is glutamate.

In certain embodiments, $X_1$, $X_2$, and $X_3$ are glutamate, aspartate, and aspartate, respectively and $X_4$ and $X_5$ are absent. In certain embodiments, $X_1$, $X_2$, and $X_3$ are glutamate, aspartate, and aspartate, respectively; $X_4$ and $X_5$ are absent; and $X_{13}$ is glutamate.

In certain embodiments, $X_1$, $X_2$, and $X_3$ are each glutamate and $X_4$ and $X_5$ are absent. In certain embodiments, $X_1$, $X_2$, and $X_3$ are each glutamate; $X_4$ and $X_5$ are absent; and $X_{13}$ is glutamate.

In certain embodiments, $X_1$ is absent; $X_2$, and $X_3$ are from aspartate; and $X_4$ and $X_5$ are absent. In certain embodiments, $X_1$ is absent; $X_2$, and $X_3$ are from aspartate; $X_4$ and $X_5$ are absent; and $X_{13}$ is glutamate.

In certain embodiments, $X_1$ is absent; $X_2$, and $X_3$ are aspartate; and $X_4$ and $X_5$ alanine and valine, respectively. In certain embodiments, $X_1$ is absent; $X_2$, and $X_3$ are aspartate; $X_4$ and $X_5$ alanine and valine, respectively; and $X_{13}$ is glutamate.

In certain embodiments, $X_6$ is tryptophan or phenyl alanine. In certain embodiments, $X_6$ is tryptophan or phenyl alanine; and $X_{13}$ is glutamate.

In certain embodiments, $X_7$ and $X_8$ are independently threonine, valine, isoleucine, leucine, arginine, or glutamate.

In certain embodiments, $X_7$ and $X_8$ are independently threonine, valine, isoleucine, leucine, arginine, or glutamate; and $X_{13}$ is glutamate.

In certain embodiments, $X_9$ is phenylalanine, valine, leucine, or isoleucine. In certain embodiments, $X_9$ is phenylalanine, valine, leucine, or isoleucine; and $X_{13}$ is glutamate.

In certain embodiments, $X_{10}$, $X_{11}$, and $X_{12}$ are independently glutamate, aspartate, glutamine, serine, or threonine. In certain embodiments, $X_{10}$, $X_{11}$, and $X_{12}$ are independently glutamate, aspartate, glutamine, serine, or threonine; and $X_{13}$ is glutamate In certain embodiments, $X_1$, $X_2$, and $X_3$ are each glutamate and $X_4$ and $X_5$ are absent; $X_4$ and $X_5$ alanine and valine, respectively; $X_6$ is tryptophan; $X_7$ and $X_8$ are independently valine or isoleucine; $X_9$ is valine; and $X_{10}$, $X_{11}$, and $X_{12}$ are independently glutamate, aspartate, or serine. In certain embodiments, $X_1$, $X_2$, and $X_3$ are each glutamate and $X_4$ and $X_5$ are absent; $X_4$ and $X_5$ alanine and valine, respectively; $X_6$ is tryptophan; $X_7$ and $X_8$ are independently valine or isoleucine; $X_9$ is valine; $X_{10}$, $X_{11}$, and $X_{12}$ are independently glutamate, aspartate, or serine; and $X_{13}$ is glutamate.

In certain embodiments, $X_1$, $X_2$, and $X_3$ are each glutamate and $X_4$ and $X_5$ are absent; or $X_1$, $X_2$, and $X_3$ are aspartate, glutamate, and glutamate, respectively and $X_4$ and $X_5$ are absent; $X_6$ is tryptophan; $X_7$ and $X_8$ are independently valine, isoleucine, or leucine; $X_9$ is valine or leucine; and $X_{10}$, $X_{11}$, and $X_{12}$ are independently glutamate, aspartate, glutamine, threonine, or serine. In certain embodiments, $X_1$, $X_2$, and $X_3$ are each glutamate and $X_4$ and $X_5$ are absent; or $X_1$, $X_2$, and $X_3$ are aspartate, glutamate, and glutamate, respectively and $X_4$ and $X_5$ are absent; $X_6$ is tryptophan; $X_7$ and $X_8$ are independently valine, isoleucine, or leucine; $X_9$ is valine or leucine; $X_{10}$, $X_{11}$, and $X_{12}$ are independently glutamate, aspartate, glutamine, threonine, or serine; and $X_{13}$ is glutamate.

In certain embodiments, $X_1$, $X_2$, and $X_3$ are glutamate, aspartate, and aspartate, respectively and $X_4$ and $X_5$ are absent; or $X_1$, $X_2$, and $X_3$ are glutamate, aspartate, and glutamate, respectively and $X_4$ and $X_5$ are absent; $X_6$ is tryptophan; $X_7$ and $X_8$ are independently valine, isoleucine, threonine, or glutamate; $X_9$ is phenylalanine; and $X_{10}$, $X_{11}$, and $X_{12}$ are independently lysine, glutamate, asparagine, aspartate, threonine, or serine. In certain embodiments, $X_1$, $X_2$, and $X_3$ are glutamate, aspartate, and aspartate, respectively and $X_4$ and $X_5$ are absent; or $X_1$, $X_2$, and $X_3$ are glutamate, aspartate, and glutamate, respectively and $X_4$ and $X_5$ are absent; $X_6$ is tryptophan; $X_7$ and $X_8$ are independently valine, isoleucine, threonine, or glutamate; $X_9$ is phenylalanine; $X_{10}$, $X_{11}$, and $X_{12}$ are independently lysine, glutamate, asparagine, aspartate, threonine, or serine; and $X_{13}$ is glutamate.

In certain embodiments, $X_1$, $X_2$, and $X_3$ are glutamate, aspartate, and aspartate, respectively and $X_4$ and $X_5$ are absent; $X_6$ is tryptophan; $X_7$ and $X_8$ are independently isoleucine, threonine, or glutamate; $X_9$ is phenylalanine; and $X_{10}$, $X_{11}$, and $X_{12}$ are independently glutamate or serine. In certain embodiments, $X_1$, $X_2$, and $X_3$ are glutamate, aspartate, and aspartate, respectively and $X_4$ and $X_5$ are absent; $X_6$ is tryptophan; $X_7$ and $X_8$ are independently isoleucine, threonine, or glutamate; $X_9$ is phenylalanine; $X_{10}$, $X_{11}$, and $X_{12}$ are independently glutamate or serine; and $X_{13}$ is glutamate.

In certain embodiments, $X_1$, $X_2$, and $X_3$ are glutamate, aspartate, and aspartate, respectively and $X_4$ and $X_5$ are absent; $X_6$ is tryptophan; $X_7$ and $X_8$ are threonine and arginine respectively; $X_9$ is phenylalanine; and $X_{10}$, $X_{11}$, and $X_{12}$ are independently glutamate or serine. In certain embodiments, $X_1$, $X_2$, and $X_3$ are glutamate, aspartate, and aspartate, respectively and $X_4$ and $X_5$ are absent; $X_6$ is tryptophan; $X_7$ and $X_8$ are threonine and arginine respectively; $X_9$ is phenylalanine; $X_{10}$, $X_{11}$, and $X_{12}$ are independently glutamate or serine; and $X_{13}$ is glutamate Alpha helices are well known in the art, as are amino acids that have a propensity to form alpha helices. For example, the amino acids methionine, alanine, leucine, glutamate and/or lysine are known to have a high propensity to form alpha helix structures when included in peptides. Other amino acids that are known to have a propensity to form an alpha helix include phenyl alanine, glycine, tryptophan, isoleucine, and valine.

$R_1$ can be an amphipathic alpha helix. In an amphipathic alpha helix, one face of the helix comprises mainly hydrophilic amino acids and the other face of the helix comprises mainly hydrophobic amino acids. The amino acid sequence of amphipathic alpha helix can generally alternate between hydrophilic and hydrophobic residues every about 3 to 4 residues, since the alpha helix makes a turn every 3.6 amino acids.

In certain embodiments, $R_1$ is a 3, 4, 5, 6, 7, 8, 9, or 10 turn amphipathic alpha helix. In certain embodiments, the amphipathic alpha helix comprises between 7 and 36; 7 and 34; 7 and 32; 7 and 30; 7 and 28; 7 and 26; 7 and 24; 7 and 22; 7 and 20; 7 and 18; 7 and 15; 7 and 13; 7 and 11; or 7 and amino acids. In certain embodiments, the amphipathic alpha helix comprises 7, 8, 9, 10, 11, 12, 13, 14, or 15 amino acids.

In certain embodiments, $R_1$ comprises an amphipathic alpha helix comprising a sequence represented by Formula II:

$$X_{14}\text{-}X_{15}\text{-}X_{16}\text{-}X_{17}\text{-}X_{18}\text{-}X_{19}\text{-}X_{20}\text{-}X_{21} \quad \text{II}$$

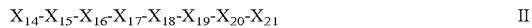

wherein $X_{14}$ and $X_{17}$ are independently an amino acid having a side chain comprising an acyclic aliphatic moiety; $X_{16}$ is an amino acid having a side chain comprising a polar moiety or is absent; $X_{15}$ and $X_{18}\text{-}X_{20}$ are independently an amino acid having a side chain comprising a polar moiety; and $X_{21}$ is an amino acid having a side chain comprising an acyclic aliphatic moiety or is absent.

In certain embodiments, $X_{14}$ and $X_{17}$ are independently alanine, leucine, isoleucine, or valine. In certain embodiments, $X_{14}$ is isoleucine or leucine. In certain embodiments, $X_{17}$ is alanine or isoleucine.

In certain embodiments, $X_{15}$ and $X_{18}\text{-}X_{20}$ are independently aspartate, arginine, glutamate, glutamine, lysine, serine, or cysteine.

In certain embodiments $X_{21}$ is alanine, leucine, or glycine.

In certain embodiments, $X_{14}$ and $X_{17}$ are independently alanine, leucine, isoleucine, or valine; $X_{15}$ and $X_{18}\text{-}X_{20}$ are independently aspartate, arginine, glutamate, glutamine, lysine, serine, or cysteine; and $X_{21}$ is alanine, leucine, or glycine.

In certain embodiments, $R_1$ comprises a peptide having at least 75%, at least 87%, or 100% sequence homology with SEQ ID NO: 17, SEQ ID NO: 18, or SEQ ID NO: 19.

In certain embodiments the recombinant peptide comprises an extended LIR motif found in AnkB or AnkG proteins from any organism including, but not limited to non-human primate, human (e.g., AnkB: SEQ ID NO:3 and AnkG: SEQ ID NO:4), mouse (e.g., AnkB: SEQ ID NO:8), rat (e.g., AnkG: SEQ ID NO:1), canine, chicken (e.g., AnkB: SEQ ID NO: 9 and AnkG: SEQ NO:5), rabbit, rat (e.g., AnkG: SEQ ID NO:1), zebra fish (e.g., AnkB SEQ ID NO:10 and AnkG: SEQ ID NO:7), frog (e.g., AnkG SEQ ID NO:6), etc.

In other embodiments, the recombinant peptide is any non-naturally occurring protein comprising a polypeptide sequence as described herein. Such peptides can be derived from proteins unrelated to AnkB and AnkG. For example, FAM134B (SEQ ID NO:21) exhibits strong binding affinities to ATG8 family members.

In certain embodiments, the recombinant peptide comprising a sequence represented by Formula I comprises a peptide having at least 88%, at least 92%, at least 97% or 100% sequence homology with SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 12, SEQ ID NO: 14, SEQ ID NO: 20, or SEQ ID NO: 21.

In certain embodiments, the recombinant peptide comprising a sequence represented by Formula I comprises a peptide having at least 88%, at least 92%, at least 97% or 100% sequence homology with SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 20, or SEQ ID NO: 21.

In certain embodiments, the recombinant peptide comprising a sequence represented by Formula I comprises a peptide having at least 88%, at least 92%, at least 97% or 100% sequence homology with SEQ ID NO: 1, SEQ ID NO: 2, or SEQ ID NO: 3.

In certain embodiments, the recombinant peptide of Formula I consists essentially of any of the peptide sequences described herein.

The recombinant peptides described herein exhibit strong binding to GABARAP, GABARAPL1, GABARAPL2, LC3A, LC3B, and LC3C. The recombinant peptides described herein can bind to GABARAP and LC3 family proteins with $K_d$ in the nanomolar and sub-nanomolar range. In certain embodiments, the recombinant peptides described herein can bind to GABARAP family members with a $K_d$ between 0.1 nM to 200 nM; 0.1 nM to 150 nM; 0.1 nM to 100 nM; 0.1 nM to 80 nM; 0.1 nM to 60 nM; 0.1 nM to 40 nM; 0.1 nM to 30 nM; 0.1 nM to 25 nM; 0.1 nM to 20 nM; 0.1 nM to 15 nM; 0.1 nM to 10 nM; or 0.1 nM to 1 nM. In certain embodiments, the recombinant peptides described herein can bind to LC3 family members with a $K_d$ between 1 nM to 100 nM; 1 nM to 75 nM; 1 nM to 50 nM; 1 nM to 25 nM; 1 nM to 20 nM; or 1 nM to 15 nM. Optionally, these values may be determined by the assays described herein and depicted in the Examples below.

In certain embodiments, the recombinant peptides described herein exhibit a $K_d$ for one or more GABARAP proteins up to 2, 3, 5, 10, 100, 500, or 1,000 times stronger than at least one LC3 protein.

The inhibitory effect of the recombinant peptides described herein may occur in a cell-free system, in cell or tissue culture and/or in a cell and/or tissue in a patient. Thus, in certain embodiments, provided is a method of inhibiting autophagy in a cell comprising the step of contacting the cell with a recombinant peptide described herein thereby inhibiting or at least partially inhibiting autophagy in the cell.

The recombinant peptides described herein can be for imaging autophagic processes by the appropriate modification of the recombinant peptide with the appropriate detectable tag. The recombinant peptides can also be modified with affinity tags, which enable the recombinant peptides to be used for pull down experiments to isolate binding targets (e.g., Atg8 proteins) involved in autophagic processes. Thus, in certain embodiments, the recombinant peptides described herein further comprise an affinity tag and/or detectable label. The affinity tag or detectable label can be covalently attached directly to the n-terminal or c-terminal of the recombinant peptide via a peptide bond or covalently attached via a linker. In alternative embodiments, affinity tag or detectable label can be covalently attached to an appropriately functionalized side chain, such as a lysine, cysteine, glutamate, aspartate, tyrosine, serine, or threonine side chain. In certain embodiments, the detectable label is covalently attached to the n-terminal of the recombinant peptide indirectly via a (Gly-Ser)$_n$ (SEQ ID NO: 27), (Gly-Gly-Gly-Ser)$_n$ (SEQ ID NO: 22), (Gly-Gly-Ser-Gly)$_n$ (SEQ ID NO: 23), (Gly-Gly-Gly-Gly-Ser)$_n$ (SEQ ID NO: 24), (Gly-Gly-Ser)n (SEQ ID NO: 28), (Gly-Ser)$_n$ (SEQ ID NO: 27) or Gly$_n$ linker (SEQ ID NO: 29), wherein n is 1-10. In certain embodiments, the detectable label is attached indirectly to the n-terminal of the recombinant peptide via a (Gly-Ser)$_n$ (SEQ ID NO: 30), (Gly-Gly-Gly-Ser)$_n$ (SEQ ID NO: 31), (Gly-Gly-Ser-Gly)$_n$ (SEQ ID NO: 32), (Gly-Gly-Gly-Gly-Ser)$_n$ (SEQ ID NO: 33), (Gly-Gly-Ser)n (SEQ ID NO: 34), (Gly-Ser)$_n$ (SEQ ID NO: 30) or Gly$_n$ linker (SEQ ID NO: 35), wherein n is 1-4. In certain embodiments, the detectable label is attached indirectly to the n-terminal of the recombinant peptide via a SGLRSGS (SEQ ID NO: 25) or YSDLDGS (SEQ ID NO: 26). In certain embodiments, the recombinant peptide further comprises a mCherry detectable label covalently attached at the n-terminal via a SGLRSGS (SEQ ID NO: 25) linker. In certain embodiments, the recombinant peptide further comprises a green fluorescent protein detectable label covalently attached at the n-terminal via an YSDLDGS (SEQ ID NO: 26) linker.

The term "affinity tag" as used herein denotes a polypeptide segment that can be attached to a one or more polypeptides to provide for, e.g., purification or detection of the one or more polypeptides. In principal, any peptide or protein for which an antibody or other specific binding agent is available can be used as an affinity tag. Affinity tags include, but are not limited to: a poly-histidine, protein, glutathione S transferase, Glu-Glu affinity tag, substance P, streptavidin binding peptide, or other antigenic epitope, such as a hemagglutinin (HA) polypeptide. See, in general, Ford et al., Protein Expression and Purification 2: 95-107, 1991.

Detectable labels can include chromogenic enzymes, radioactive isotopes, chromophores, luminescent compounds, fluorescent compounds, magnetic resonance imaging compounds, superparamagnetic particles, and ultrasmall superparamagnetic particles. In certain embodiments, the detectable label is fluorescent protein, such as green fluorescent protein or mCherry.

Suitable detectable labels include any composition detectable by spectroscopic, photochemical, biochemical, immunochemical, electrical, optical or chemical means. Suitable detectable labels include, but are not limited to, magnetic beads (e.g. Dynabeads™), fluorescent dyes (e.g., fluorescein, Texas Red, rhodamine, a green fluorescent protein, a red fluorescent protein, a yellow fluorescent protein, and the like), radiolabels (e.g., $^3$H, $^{125}$I, $^{35}$S, $^{14}$C, or $^{32}$P), enzymes (e.g., horse radish peroxidase, alkaline phosphatase, luciferase, and others commonly used in an enzyme-linked immunosorbent assay (ELISA)), and colorimetric labels such as colloidal gold or colored glass or plastic (e.g. polystyrene, polypropylene, latex, etc.) beads.

Also provided is a polynucleotide encoding a recombinant peptide as described herein. In certain embodiments, the polynucleotide encodes the recombinant peptide::fluorescent protein conjugate. The polynucleotide can be included in a plasmid expression vector. Expression of the plasmid expression vector encoding the recombinant peptide can be driven in a tissue-specific or development-stage-specific manner or induced by chemical-regulation or physical-regulation using the appropriate promoter. Any promoter known in the art can be used to drive the expression of the plasmid encoding the recombinant peptides described herein. Such promoters include, but are not limited to, nfya-1, col-19, myo-3, vha-6, hyp7, y37A1B.5 CMV, CAG, SV40, and the like.

The present disclosure also provides a pharmaceutical composition comprising any one of the recombinant peptides described herein and at least one pharmaceutically acceptable excipient.

The recombinant peptides described herein and their pharmaceutically acceptable salts are can be administered to a subject either alone or in combination with pharmaceutically acceptable carriers or diluents in a pharmaceutical composition according to standard pharmaceutical practice. The compounds can be administered orally or parenterally, preferably parenterally. Parenteral administration includes intravenous, intramuscular, intraperitoneal, subcutaneous and topical, the preferred method being intravenous administration.

Accordingly, the present disclosure provides pharmaceutically acceptable compositions, which comprise a therapeutically-effective amount of one or more of the recombinant peptides described herein, formulated together with one or more pharmaceutically acceptable carriers (additives) and/or diluents. The pharmaceutical compositions of the present disclosure may be specially formulated for administration in solid or liquid form, including those adapted for the following: (1) parenteral administration, for example, by subcutaneous, intramuscular, intravenous or epidural injection as, for example, a sterile solution or suspension, or sustained-release formulation; and (2) oral administration, for example, drenches (aqueous or non-aqueous solutions or suspensions), tablets, e.g., those targeted for buccal, sublingual, and systemic absorption, boluses, powders, granules, pastes for application to the tongue. The preferred method of administration of compounds of the present invention is parental administration (intravenous).

As set out herein, certain embodiments of the recombinant peptides described herein may contain a basic functional group, such as amino, and are, thus, capable of forming pharmaceutically-acceptable salts with pharmaceutically-acceptable acids. The term "pharmaceutically-acceptable salts" in this respect, refers to the relatively nontoxic, inorganic and organic acid addition salts of compounds of the present disclosure. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like.

The pharmaceutically acceptable salts of the recombinant peptides of the present disclosure include the conventional nontoxic salts or quaternary ammonium salts of the compounds, e.g., from nontoxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the recombinant peptides described herein may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

Wetting agents, emulsifiers and lubricants, such as sodium lauryl sulfate and magnesium stearate, as well as coloring agents, release agents, coating agents, sweetening, flavoring and perfuming agents, preservatives, solubilizing agents, buffers and antioxidants can also be present in the compositions.

Methods of preparing these formulations or recombinant peptides include the step of bringing into association a recombinant peptide described herein with the carrier and, optionally, one or more accessory ingredients. In general, the formulations are prepared by uniformly and intimately bringing into association a compound of the present invention with liquid carriers (liquid formulation), liquid carriers followed by lyophylization (powder formulation for reconstitution with sterile water or the like), or finely divided solid carriers, or both, and then, if necessary, shaping or packaging the product.

Pharmaceutical compositions of the present disclosure suitable for parenteral administration comprise one or more recombinant peptides described herein in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, chelating agents, solutes which render the formulation isotonic with the blood of the intended recipient or suspending or thickening agents. In the examples, the active ingredients are brought together with the pharmaceutically acceptable carriers in solution and then lyophilized to yield a dry powder. The dry powder is packaged in unit dosage form and then reconstituted for parental administration by adding a sterile solution, such as water or normal saline, to the powder.

Examples of suitable aqueous and non-aqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants, such as preservatives, wetting agents, emulsifying agents and dispersing agents. Prevention of the action of microorganisms upon the recombinant peptides of the present disclosure may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

The recombinant peptides described herein are potent inhibitors of Atg8 and thus can be used to treat a disease or condition in which inhibition of autophagy has a therapeutic effect. Thus, in certain embodiments, provided herein is a method of inhibiting autophagy in a subject for whom inhibition of autophagy is beneficial, comprising administering to the subject a therapeutically effective amount of the recombinant peptide described herein thereby inhibiting autophagy activity in the subject. Such disease diseases or conditions in which inhibition of autophagy is beneficial include, but are not limited to cancer (e.g. breast, ovarian and prostate cancers), metabolic diseases (e.g. atherosclerosis, and diabetes), immunity disorders (e.g. celiac disease, multiple sclerosis) and neurodegenerative diseases (e.g. alzheimer's Diseases, Parkinson diseases).

Inhibition of autophagy has been proposed to be a new anticancer therapy by promoting radiosensitization and chemosensitization. Thus, the recombinant peptides described herein can be used to sensitize tumors to cancer drugs and/or radiation therapy. Accordingly, the recombinant peptides described herein can be co-administered with one or more cancer drugs to treat subjects suffering from cancer.

A recombinant peptide described and a cancer drug may be administered concurrently (e.g., simultaneously, essentially simultaneously or within the same treatment protocol) or sequentially, depending upon the nature of the cancer, the condition of the patient, and the actual choice of cancer drug to be administered in conjunction (i.e., within a single treatment protocol) with a recombinant peptide described herein.

If a recombinant peptide described herein and the cancer drug are not administered simultaneously or essentially simultaneously, then the optimum order of administration of the recombinant peptide described herein and the cancer drug, may be different for different types of cancer. Thus, in certain situations the recombinant peptide described herein may be administered first followed by the administration of the cancer drug; and in other situations the cancer drug may be administered first followed by the administration of a recombinant peptide described herein. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient.

EXAMPLES

Ank-Derived Peptides can Potently Inhibit Autophagy in Heterologous Cells

Figure 6:
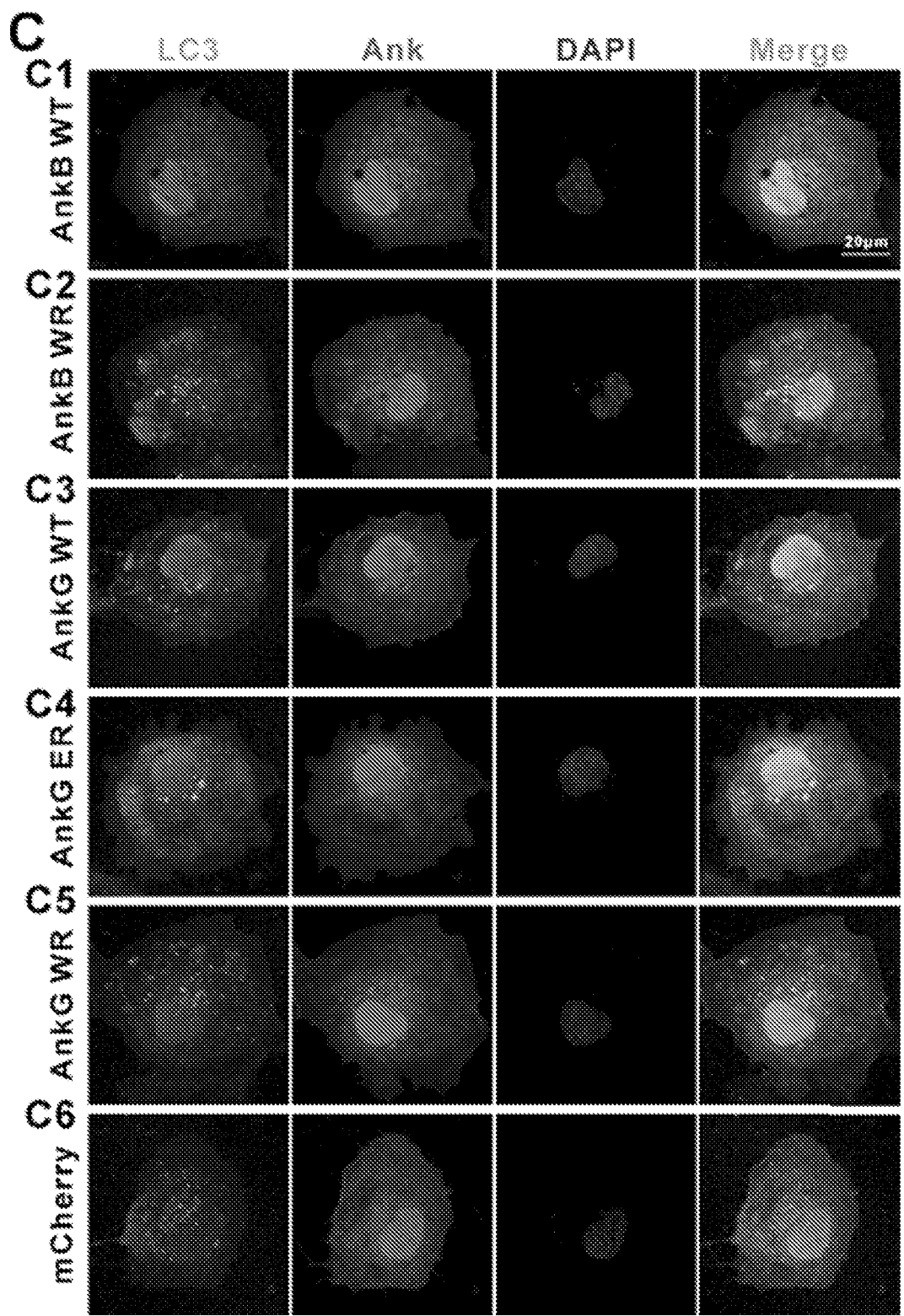
FIG. 6A depicts the amino acid sequences of the AnkB WT (SEQ ID NO: 3), AnkB W1592R (SEQ ID NO: 11), AnkG WT (SEQ ID NO: 1), AnkG E1991R (SEQ ID NO: 2), and AnkG W1989R (SEQ ID NO: 13) used in the cell culture and C. elegans studies below.
FIG. 6B summarizes $K_d$ values of the bindings between the AnkB WT (SEQ ID NO: 3), AnkB W1592R (SEQ ID NO: 11), AnkG WT (SEQ ID NO: 1), AnkG E1991R (SEQ ID NO: 2), and AnkG W1989R (SEQ ID NO: 13) and different Atg8 family members.
FIG. 6C depicts representative fluorescence microscopy images of LC3-positive puncta in COS-7 cells expressing different mCherry-tagged AnkB/G peptides. C1: mCherry only; C2: mCherry::AnkB WT (SEQ ID NO: 3); C3: mCherry::AnkB W1592R (SEQ ID NO: 11); C4: mCherry::AnkG WT (SEQ ID NO: 1); C5: mCherry::AnkG E1991R (SEQ ID NO: 2); and C6: mCherry::AnkG W1989R (SEQ ID NO: 13).
FIG. 6D depicts a graph quantifying the number of LC3-positive puncta in COS7 cells expressing mCherry only; mCherry::AnkB WT (SEQ ID NO: 3); mCherry::AnkB W1592R (SEQ ID NO: 11); mCherry::AnkG WT (SEQ ID NO: 1); mCherry::AnkG E1991R (SEQ ID NO: 2); and mCherry::AnkG W1989R (SEQ ID NO: 13). Data were expressed as mean±SEM; ns: not significant, p>0.05; *: p≤0.05; : p≤0.01; *: p≤0.001; ****: p≤0.0001.
FIG. 6E depicts representative fluorescence microscopy images and GABARAP-positive puncta in COS-7 cells expressing different mCherry-tagged AnkB/G peptides. E1: mCherry only; E2: mCherry::AnkB WT (SEQ ID NO: 3); E3: mCherry::AnkB W1592R (SEQ ID NO: 11); E4: mCherry::AnkG WT (SEQ ID NO: 1); E5: mCherry::AnkG E1991R (SEQ ID NO: 2); and E6: mCherry::AnkG W1989R (SEQ ID NO: 13).
FIG. 6F depicts a graph quantifying the number of GABARAP-positive puncta in COS7 cells expressing mCherry only; mCherry::AnkB WT (SEQ ID NO: 3); mCherry::AnkB W1592R (SEQ ID NO: 11); mCherry::AnkG WT (SEQ ID NO: 1); mCherry::AnkG E1991R (SEQ ID NO: 2); and mCherry::AnkG W1989R (SEQ ID NO: 13). Data were expressed as mean±SEM; ns: not significant, p>0.05; *: p≤0.05; : p≤0.01; *: p≤0.001; ****: p≤0.0001.
FIG. 6G depicts a graph quantifying the number of p62-positive puncta in COS7 cells expressing mCherry only; mCherry::AnkB WT (SEQ ID NO: 3); mCherry::AnkB W1592R (SEQ ID NO: 11); mCherry::AnkG WT (SEQ ID NO: 1); mCherry::AnkG E1991R (SEQ ID NO: 2); and mCherry::AnkG W1989R (SEQ ID NO: 13). Data were expressed as mean±SEM; ns: not significant, p>0.05; *: p≤0.05; : p≤0.01; *: p≤0.001; ****: p≤0.0001.
Figure 6:
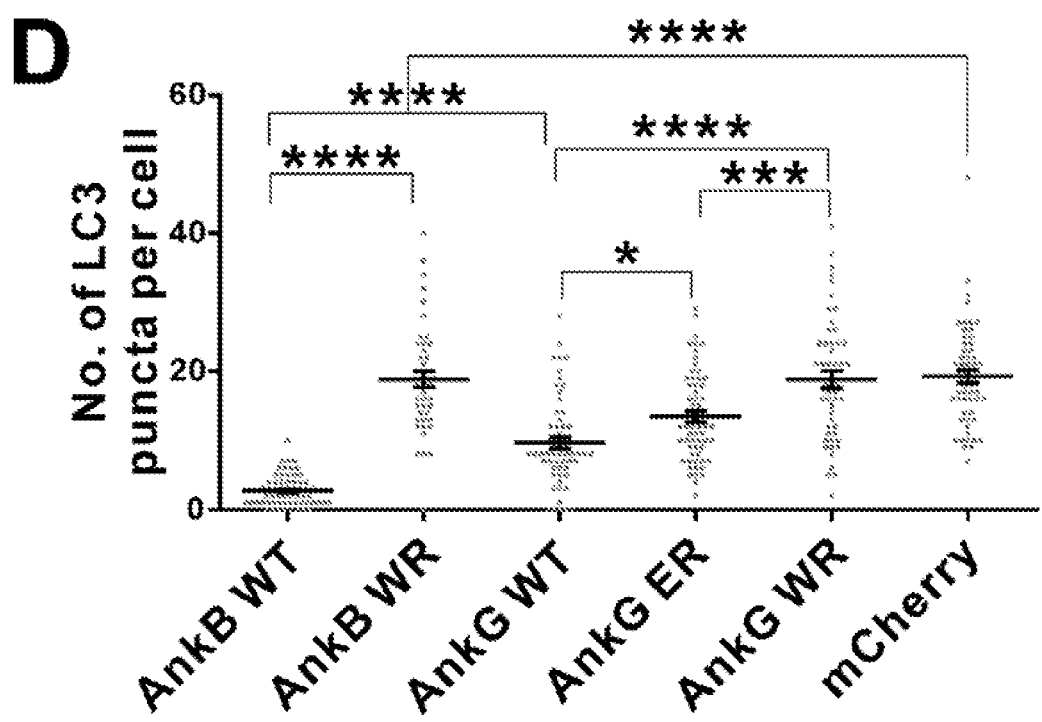
Figure 6:
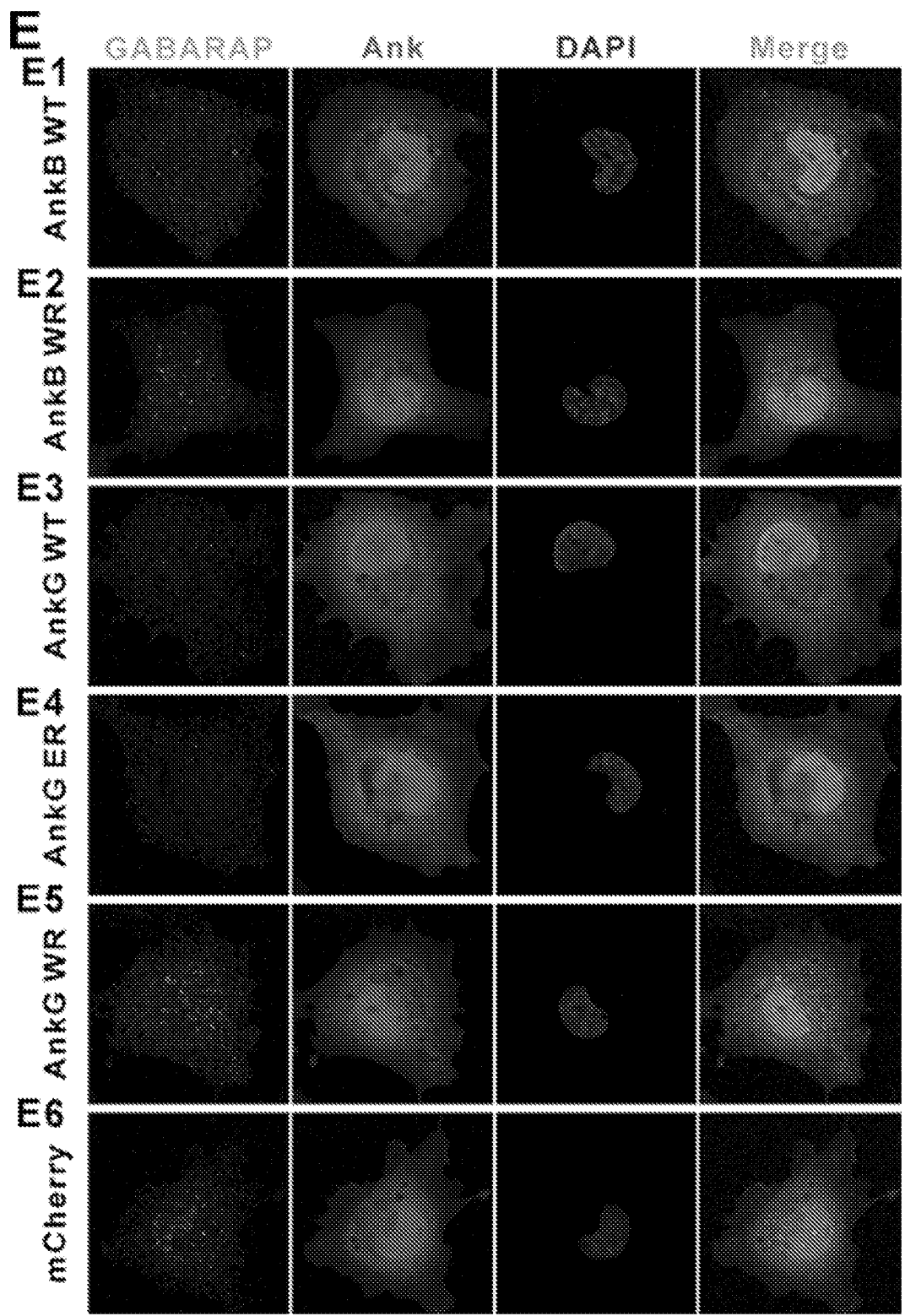
Figure 6:
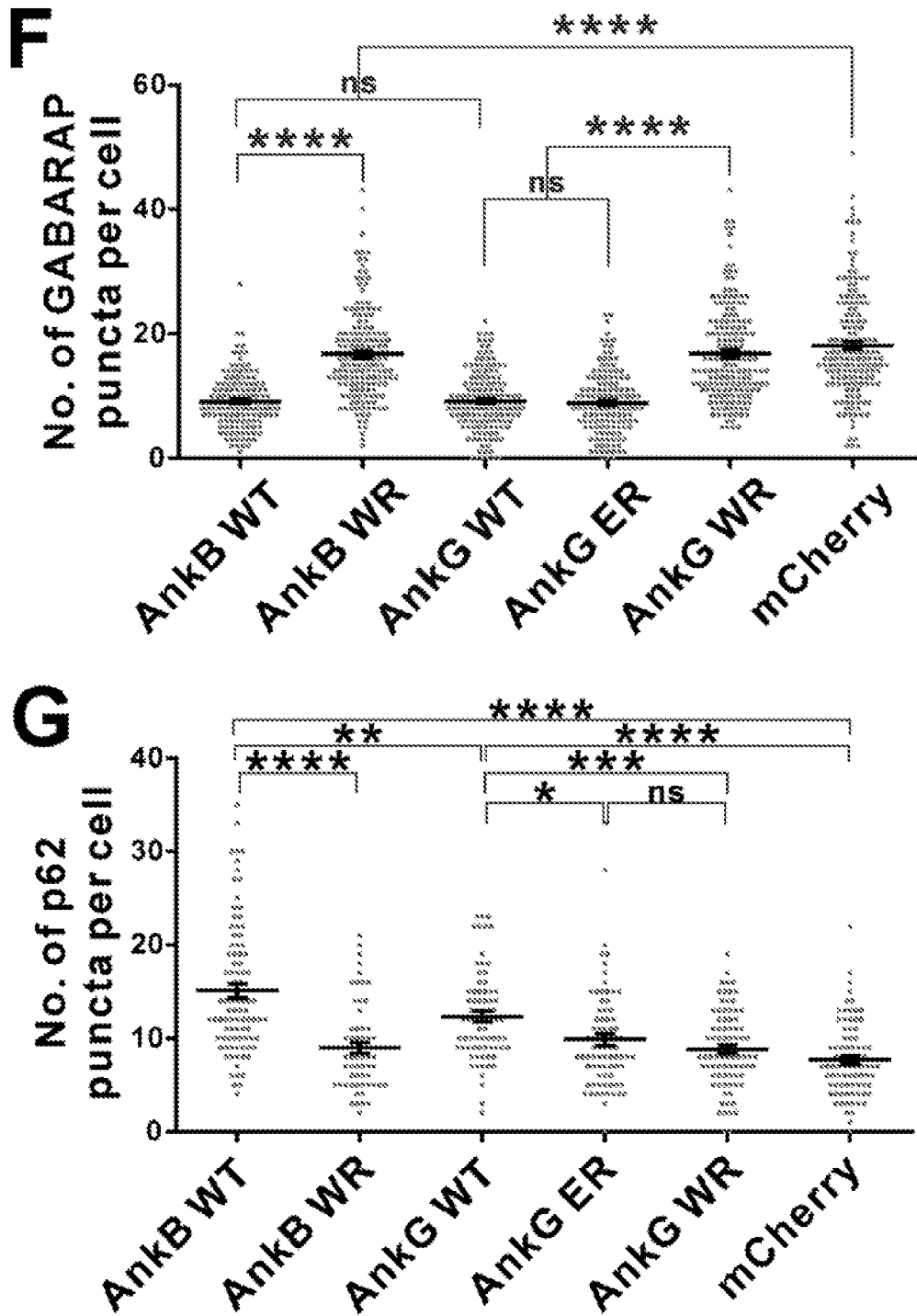

We used the well-established cultured COS7 cells for assessing autophagy inhibitions by the AnkB/G LIR peptides over-expressed in the cells. We quantified the numbers of endogenous LC3- or GABARAP-positive puncta, which represent LC3 or GABARAP-containing autophagic structures, as readouts to quantify autophagy inhibitions (Klionsky et al., 2016; Mizushima et al., 2010). After nutrients deprivation, obvious accumulations of LC3- or GABARAP-positive puncta could be observed in cells over-expressing mCherry only, indicating induction of autophagy by starvation (FIG. 6C&E6). Over-expression of the mCherry-AnkB WT reduced the LC3- and GABARAP-puncta to the background level (i.e. the level of LC3- and GABARAP-puncta when cells were not starved, data not shown). In contrast, expression of the mCherry-AnkB WR peptide had no impact on the LC3- or GABARAP-puncta numbers (i.e. with the same puncta numbers as expressing the mCherry vector control; FIG. 6C-F). The above results suggest that the AnkB WT peptide can function as a potent autophagy inhibitor by targeting all Atg8 family members.

Entirely consistent with our biochemical data, the AnkG WT peptide potently inhibited GABARAP puncta formation, but only modestly reduced LC3-positive puncta when over-expressed in COS7 cells. Satisfyingly, the AnkG ER peptide had essentially no impact on the LC3 puncta number reduction, but potently inhibited the GABARAP puncta formation (FIG. 6C-F), indicating that the AnkG ER peptide can indeed function as a specific GABARAP-mediated autophagy inhibitor. As a negative and specificity control, we did not see any noticeable changes in the LC3- or GABARAP-puncta numbers when cells were over-expressed with the mCherry-AnkG WR peptide (FIG. 6C-F).

Figure 7:
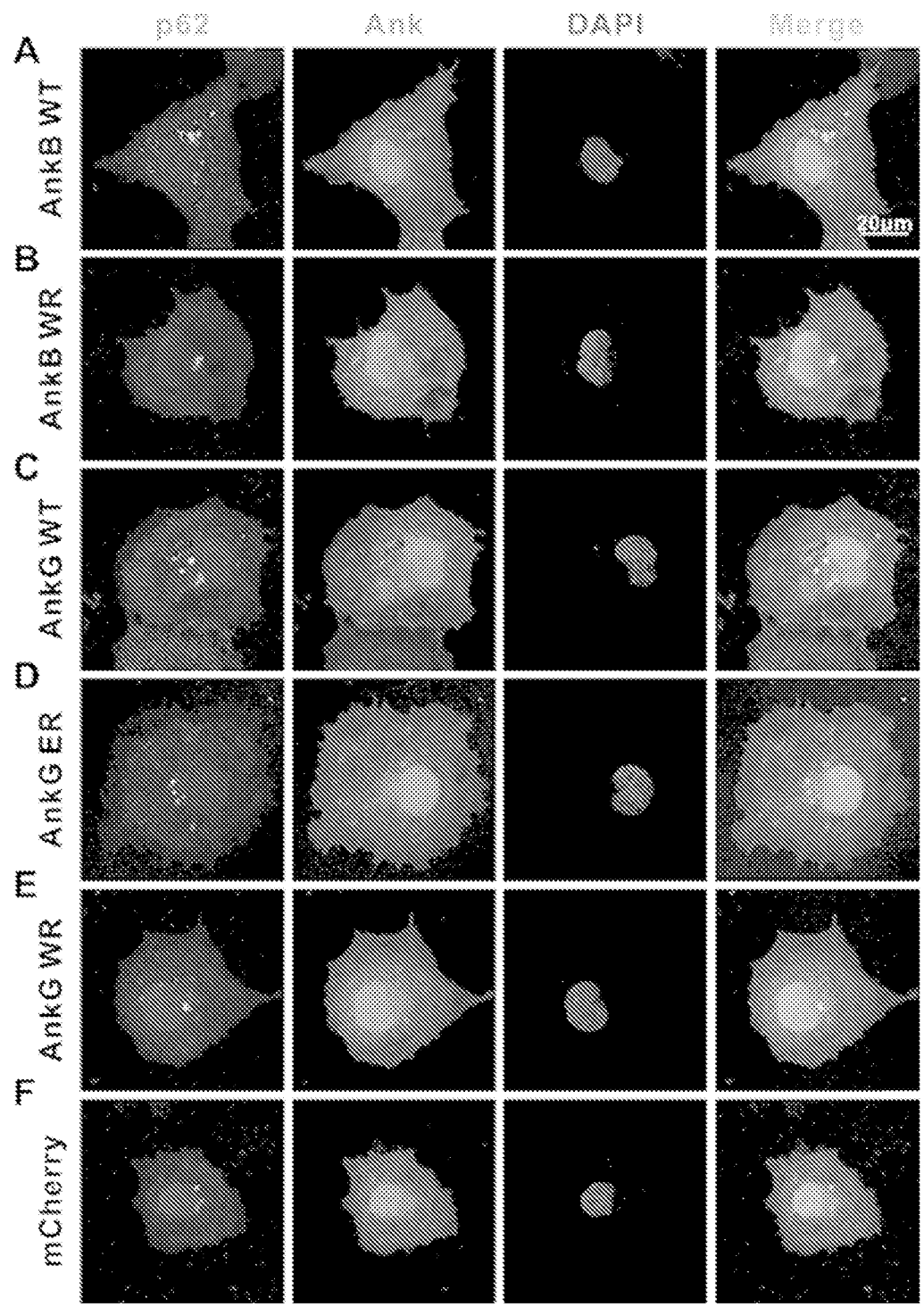
FIG. 7A depicts representative fluorescence microscopy images showing the p62-positive puncta in COS7 cells expressing mCherry::AnkB WT (SEQ ID NO: 3). Scale bar: 20 µm.
FIG. 7B depicts representative fluorescence microscopy images showing the p62-positive puncta in COS7 cells expressing mCherry::AnkB W1592R (SEQ ID NO: 11). Scale bar: 20 µm.
FIG. 7C depicts representative fluorescence microscopy images showing the p62-positive puncta in COS7 cells mCherry::AnkG WT (SEQ ID NO: 1). Scale bar: 20 µm.
FIG. 7D depicts representative fluorescence microscopy images showing the p62-positive puncta in COS7 cells expressing mCherry::AnkG E1991R (SEQ ID NO: 2). Scale bar: 20 µm.
FIG. 7E depicts representative fluorescence microscopy images showing the p62-positive puncta in COS7 cells expressing mCherry::AnkG W1989R (SEQ ID NO: 13). Scale bar: 20 µm.
FIG. 7F depicts representative fluorescence microscopy images showing the p62-positive puncta in COS7 cells expressing mCherry only. Scale bar: 20 µm.

We further quantified the level of p62, one of the best studied selective autophagy substrates, to monitor the autophagic flux in COS7 cells expressing various AnkB/G LIR peptides under the starvation condition (Klionsky et al., 2016; Mizushima et al., 2010). Upon autophagy induction, p62 forms aggregates via its LIR motif-mediated interactions to Atg8s and subsequent incorporation into autophagosomes (Bjorkoy et al., 2005; Pankiv et al., 2007). Only a relatively low and steady level of p62 aggregates is formed if autophagy flux is normal (i.e. p62-positive autophagosomes are steadily cleared by fusing with lysosomes; (Bjorkoy et al., 2005)), and this is indeed the case when cells were expressed with the mCherry vector control (FIG. 7F). Over-expression of the AnkB WT peptide dramatically increased the p62-positive puncta (FIGS. 7&6G), presumably due to the potent inhibitions of all Atg8-mediated autophagy processes. Interestingly, although the AnkG WT peptide also obviously increased p62-positive puncta in COS7 cells, the number of the p62 puncta increase is nevertheless significantly lower than those induced by the AnkB WT peptide (FIG. 6G), indicating that a portion of LC3 subfamily-mediated autophagy was not blocked by the AnkG WT peptide. As we have expected, neither of the AnkB/G WR peptides could induce p62-positive puncta increase when compared to the mCherry vector control (FIGS. 7&6G). Satisfyingly, there was no statistically significant increase of p62-positive puncta in cells expressing the AnkG ER peptide compared to the cells expressing mCherry or AnkB/G WR (FIGS. 7&6G). This is consistent with a previous siRNA-based study showing that knockdown of LC3 but not GABARAP causes p62 accumulation in COS7 cells (Maruyama et al., 2014). Taken together, the above cell-based assays reinforce our earlier conclusion derived from biochemical and structural studies, that the AnkB WT peptide can function as potent autophagy inhibitor by targeting all members of the Atg8 family and the AnkG WT or ER peptides can selectively target the GABARAPs and spare the LC3s.

Expression of the Ank-Derived Peptides Impairs Autophagy in C. elegans

C. elegans provides an ideal platform to study autophagy and especially to investigate roles of different members of Atg8 in autophagy, because worms contain both GABARAP and LC3 subfamily Atg8s and yet simple enough with one gene for each subfamily (worm lgg-1 and lgg-2 are mammalian orthologues of GABARAP and LC3, respectively). It has also been shown earlier on that lgg-1 and lgg-2 act non-redundantly in autophagy (Wu et al., 2015). Prior to performing autophagy assays in worms, we measured the bindings of various AnkB/G LIR peptides to purified LGG-1 and LGG-2 using the same method as we have described for FIGS. 1&3. In parallel to what we found in the bindings to mammalian Atg8s, the AnkB WT peptide binds very strongly to both LGG-1 and LGG-2, and the WR mutant peptide eliminated the bindings (FIG. 6B; bottom two rows). The AnkG WT peptide binds strongly to LGG-1 but with an about 130-fold weaker affinity towards LGG-2. The AnkG ER peptide retained strong binding to LGG-1 and displayed ~1,000-fold weaker binding to LGG-2 (FIG. 6B; bottom two rows).

Figure 8:
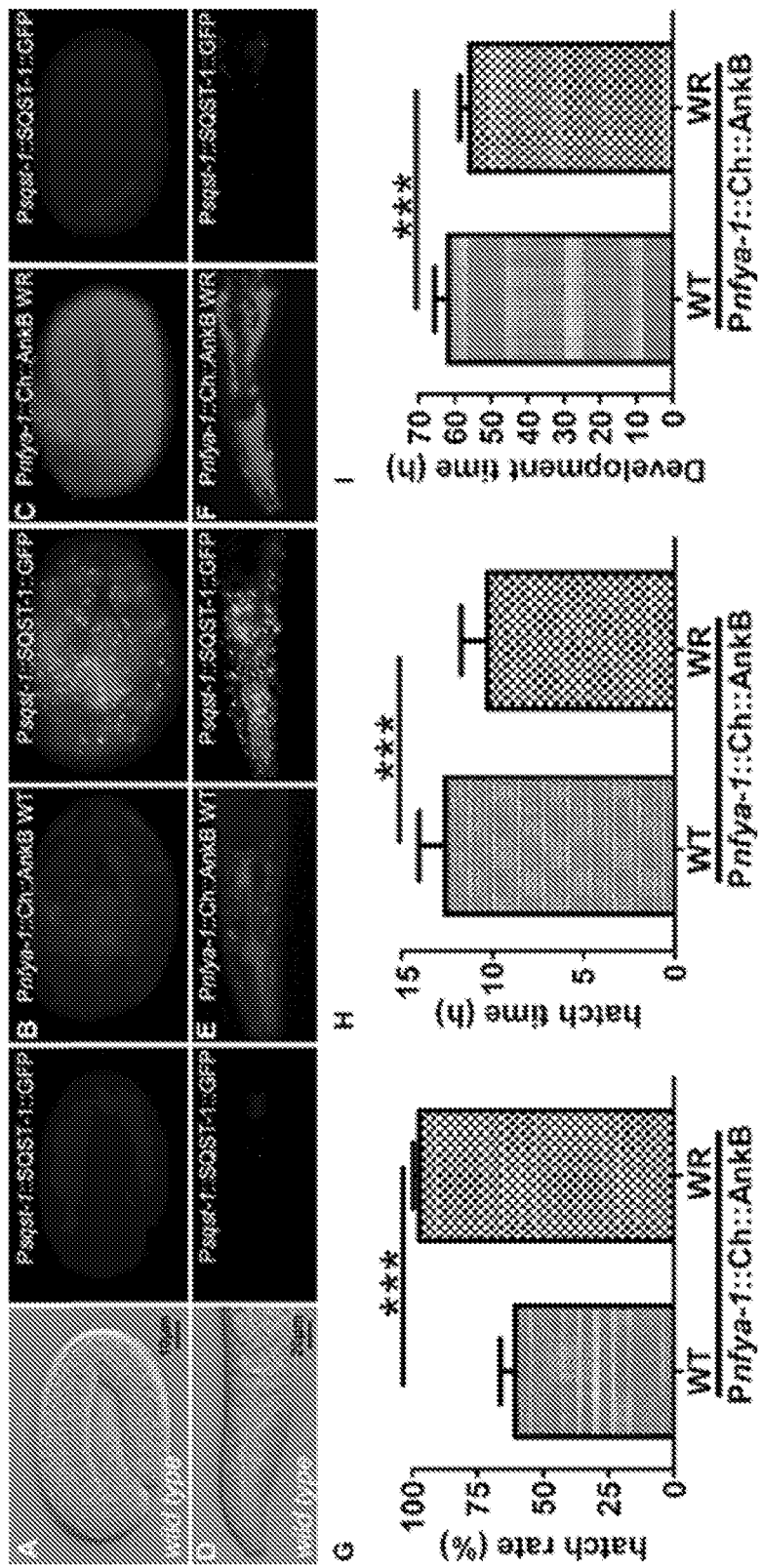
FIG. 8A depicts a differential interference contrast microscopy image of a C. elegans wild-type embryo (left panel) and a fluorescence microscopy photograph showing fluorescence from SQST-1::GFP, which is weakly expressed and diffusely localized in the cytoplasm. Scale bar 10 µm.
FIG. 8B depicts a fluorescence microscopy image of a C. elegans embryo expressing Cherry::AnkB WT (SEQ ID NO: 3) recombinant peptide (left panel) having a large number of SQST-1::GFP aggregates accumulated in the embryos (right panel).
FIG. 8C depicts a fluorescence microscopy image of a C. elegans embryo expressing Cherry::AnkB W1592R (SEQ ID NO: 11) (left panel) showing no SQST-1::GFP aggregates (right panel).
FIG. 8D depicts a differential interference contrast microscopy image of a C. elegans wild-type larvae and a fluorescence microscopy image showing fluorescence from SQST-1::GFP, which is weakly expressed and diffusely localized in the cytoplasm (right panel). Scale bar 20 µm.
FIG. 8E depicts a fluorescence microscopy image of a C. elegans larvae expressing Cherry::AnkB WT (SEQ ID NO: 3) recombinant peptide (left panel) having a large number of SQST-1::GFP aggregates at the larval and adult stages (right panel).
FIG. 8F depicts a fluorescence microscopy image of a C. elegans larvae expressing Cherry::AnkB W1592R (SEQ ID NO: 11) (left panel) showing no SQST-1::GFP aggregates (right panel).
FIG. 8G depicts a bar graph showing the hatch rate of C. elegans embryos expressing Pnfya-1::ch::AnkB WT (SEQ ID NO: 3) (n=236) and Pnfya-1::ch::AnkB W1592R (SEQ ID NO: 11) (n=207). Data are shown as mean±SD, ***p<0.0001.
FIG. 8H depicts a bar graph showing the time for embryos expressing Pnfya-1::ch::AnkB WT (SEQ ID NO: 3) (n=13) and Pnfya-1::ch::AnkB W1592R (SEQ ID NO: 11) (n=14) to develop into L1 larvae. Data are shown as mean±SD, ***p<0.0001.
FIG. 8I depicts a bar graph showing the time for L1 larvae expressing Pnfya-1::ch::AnkB WT (SEQ ID NO: 3) (n=13) and Pnfya-1::ch::AnkB W1592R (SEQ ID NO: 11) (n=14) to develop into young adults. Data are shown as mean±SD, ***p<0.0003.

We next determined whether the AnkB WT peptide blocks autophagy in C. elegans. Autophagy is required for degradation of a variety of protein substrates, including the C. elegans p62 homolog SQST-1 during development (Tian et al., 2010). In the wild type animals, SQST-1::GFP is weakly expressed and diffusely localized in the cytoplasm, while numerous SQST-1 aggregates accumulate in autophagy mutants (Tian et al., 2010). The AnkB WT peptide fused with the Cherry reporter (Cherry::AnkB WT) or Cherry::AnkB WR was expressed under the control of the nfya-1 promoter, which is expressed ubiquitously from the embryonic to adult stages. The expression plasmids were injected into animals carrying integrated SQST-1::GFP reporter (bpIs151) and transgenic lines were obtained and analyzed. We found that animals expressing Cherry::AnkB WT accumulated a large number of SQST-1::GFP aggregates in multiple tissues from the embryonic to adult stages (FIGS. 8A, B, D&E). In contrast, no SQST-1::GFP aggregates were formed in animals expressing Cherry::AnkB WR (FIG. 8C, F).

Autophagy plays critical roles in various physiological processes occurring during development or in adult C. elegans (Zhang et al., 2015). Fewer autophagy mutants develop into larvae. Animals expressing Pnfya-1::Cherry::AnkB WT showed a significant reduction in hatching rate. 60.8% embryos expressing the AnkB WT peptide hatched, compared to 96.9% of embryos expressing AnkB WR (FIG. 8G). Autophagy mutants also grow slowly. Compared to embryos expressing AnkB WR mutant peptide, embryos expressing Cherry::AnkB WT took approximately two more hours to develop into L1 larvae, and 6 more hours to develop into young adults (FIGS. 8H&I). Thus, the AnkB WT peptide blocks autophagy during *C. elegans* development.

Similarly, we also tested the blocking effect of AnkG peptides in *C. elegans*. Under control of hyp7 promoter, the epidermis expressing Cherry::AnkG WT or ER peptides rather than Cherry::AnkG WR peptide caused accumulation of SQST-1::GFP aggregates from the embryonic to adult stages (FIG. 10A-H). This observation is somewhat different from that in mammalian heterologous cells. This may be explained by the different roles of the two families in different organisms. In mammal, p62 degradation is dependent on LC3 but not GABARAP (Maruyama et al., 2014), so blocking GABARAP binding has minimal effect on p62 degradation. However, in *C. elegans*, LGG-1 acts upstream to LGG-2 (Manil-Segalen et al., 2014; Wu et al., 2015), so blocking either of them will lead to defect in SQST-1 degradation.

Figure 9:
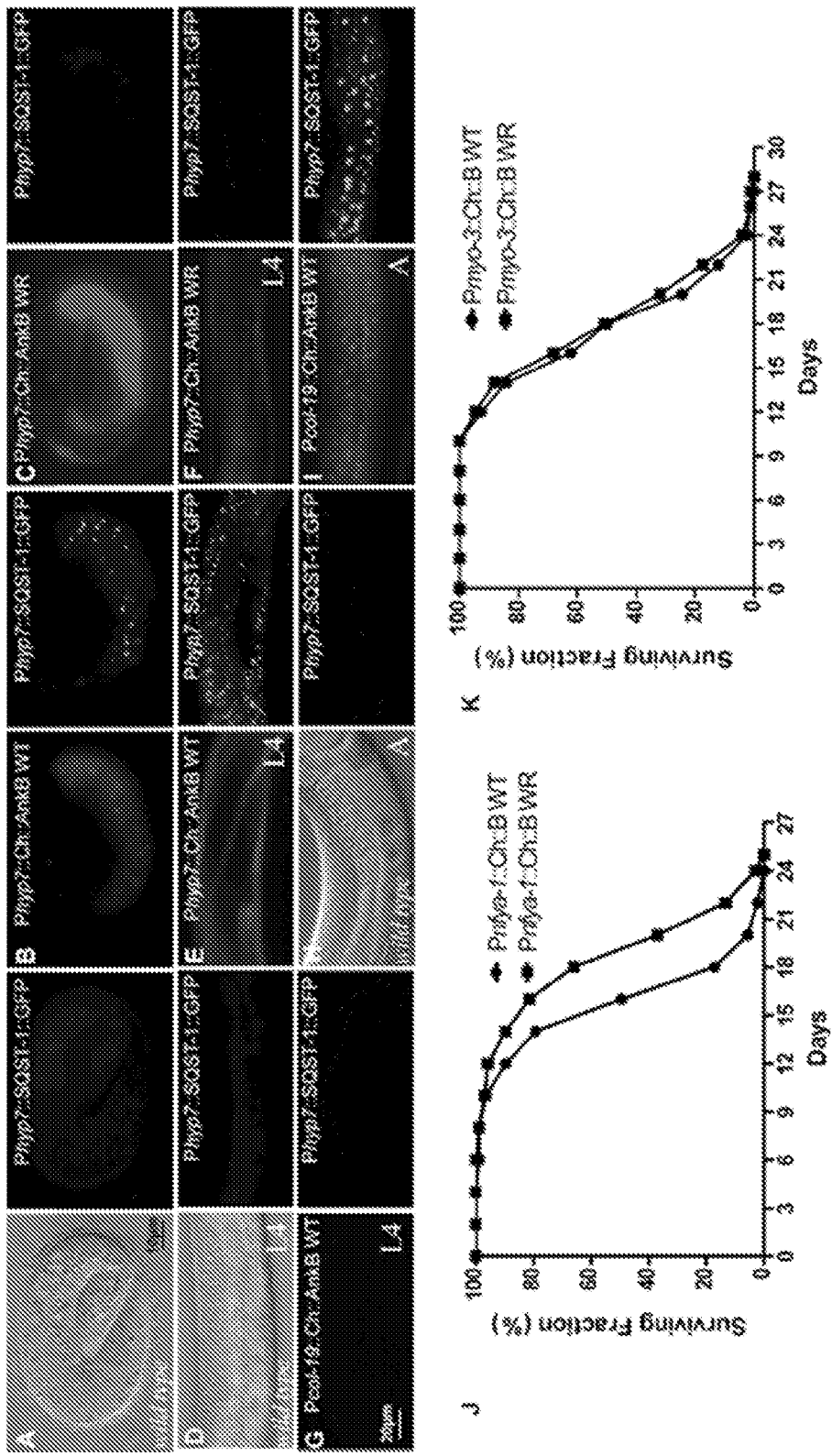
FIG. 9A depicts a differential interference contrast microscopy image of a C. elegans wild-type embryo (left panel) and a fluorescence microscopy image showing fluorescence from SQST-1::GFP, which is weakly expressed and diffusely localized in hypodermis (right panel).
FIG. 9B depicts a fluorescence microscopy image of a C. elegans embryo.
expressing mCherry::AnkB WT (SEQ ID NO: 3) (left panel) showing a large number of SQST-1::GFP aggregates accumulate in hypodermal cells in embryos (right panel).
FIG. 9C depicts a fluorescence microscopy image of a *C. elegans* embryo expressing mCherry::AnkB W1592R (SEQ ID NO: 11) (left panel) showing no SQST-1::GFP aggregates (right panel).
FIG. 9D depicts a differential interference contrast microscopy image of a *C. elegans* wild-type L4 larvae (left panel) and a fluorescence microscopy image showing fluorescence from SQST-1::GFP, which is weakly expressed and diffusely localized in hypodermis (right panel).
FIG. 9E depicts a fluorescence microscopy image of a *C. elegans* wild-type L4 larvae expressing mCherry::AnkB WT (SEQ ID NO: 3) (left panel) showing a large number of SQST-1::GFP aggregates accumulate in the hypodermis (right panel).
FIG. 9F depicts a fluorescence microscopy image of a *C. elegans* wild-type L4 larvae expressing mCherry::AnkB W1592R (SEQ ID NO: 11) (left panel) showing no SQST-1::GFP aggregates (right panel).
FIG. 9G depicts a fluorescence microscopy image of a *C. elegans* L4 larvae expressing mCherry::AnkB WT (SEQ ID NO: 3) driven by the col-19 promoter, which is specifically expressed in hypodermal cells from the young adult stage onwards (left panel) showing no expression of mCherry::AnkB WT (SEQ ID NO: 3) in the larval stage and no SQST-1::GFP aggregates (right panel).
FIG. 9H depicts a differential interference contrast microscopy image of a *C. elegans* wild type adult (left panel) and a fluorescence microscopy image showing fluorescence from SQST-1::GFP, which is weakly expressed and diffusely localized in hypodermis (right panel).
FIG. 9I depicts a fluorescence microscopy image of an adult *C. elegans* expressing mCherry::AnkB WT (SEQ ID NO: 3) driven by the col-19 promoter, which is specifically expressed in hypodermal cells from the young adult stage onwards (left panel) and a fluorescence microscopy image showing fluorescence from SQST-1::GFP, which is expressed and localized in hypodermis (right panel).
FIG. 9J shows a survival curve for Pnfya-1::ch::AnkB WT and Pnfya-1::ch::AnkB WR animals. (Median lifespan is 16.32 days for animals expressing Pnfya-1::ch::AnkB WT and 19.15 days for animals expressing Pnfya-1::ch::AnkB WR; p=0.0000).
FIG. 9K shows a survival curve for Pmyo-3::ch::AnkB WT and Pmyo-3::ch::AnkB WR worms. (Median lifespan: 18.12 days for Pmyo-3::ch::AnkB WT and 18.72 days for Pmyo-3::ch::AnkB WR; p=0.3113).
Figure 10:
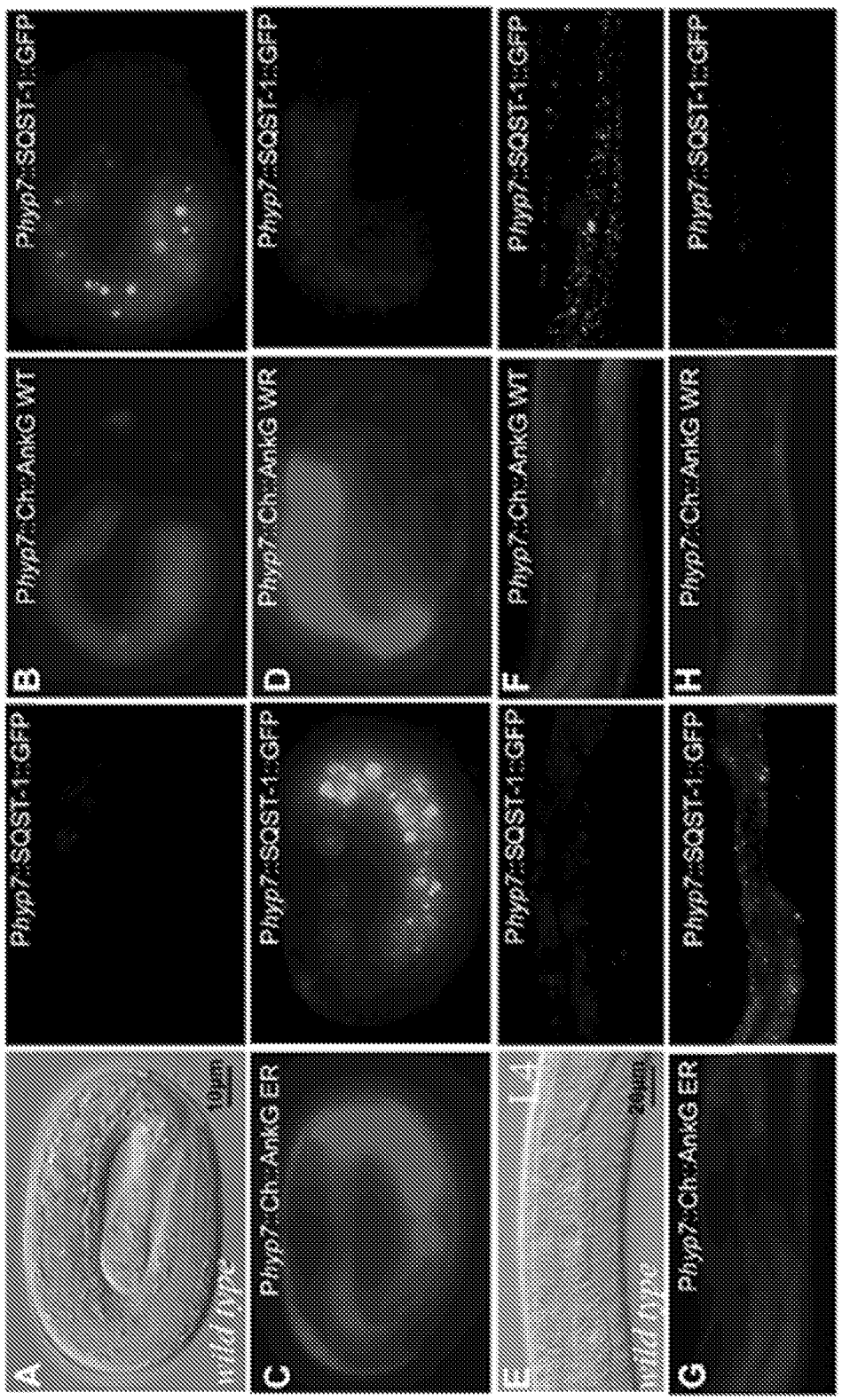
FIG. 10A depicts a differential interference contrast microscopy image of a *C. elegans* wild embryo (left panel) and a fluorescence microscopy image showing fluorescence from SQST-1::GFP, which is weakly expressed and diffusely localized in hypodermis (right panel).
FIG. 10B depicts a fluorescence microscopy image of a *C. elegans* embryo carrying expressing mCherry::AnkG WT (SEQ ID NO: 1) (left panel) results in accumulation of the SQST-1::GFP aggregates at the embryonic stage (right panel).
FIG. 10C depicts a fluorescence microscopy image of an embryo carrying expressing mCherry::AnkG E1991R (SEQ ID NO: 2) (left panel) results in the accumulation of SQST-1::GFP aggregates at the embryonic stage (right panel).
FIG. 10D depicts a fluorescence microscopy image of an embryo carrying expressing mCherry::AnkG W1989R (SEQ ID NO: 2) (left panel) results in no SQST-1::GFP aggregates at the embryonic stage (right panel).
FIG. 10E depicts a differential interference contrast microscopy image of a *C. elegans* wild-type L4 larvae carrying (left panel) and a fluorescence microscopy image showing fluorescence from SQST-1::GFP, which is weakly expressed and diffusely localized in hypodermis (right panel).
FIG. 10F depicts a fluorescence microscopy image of a *C. elegans* wild-type L4 larvae expressing Phyp7::mCherry::AnkG (SEQ ID NO: 1) (left panel) showing a large number of SQST-1::GFP aggregates accumulate in the hypodermis (right panel).
FIG. 10G depicts a fluorescence microscopy image of a *C. elegans* wild-type L4 larvae expressing Phyp7::mCherry::AnkG E1991R (SEQ ID NO: 2) (left panel) showing a large number of SQST-1::GFP aggregates accumulate in the hypodermis (right panel).
FIG. 10H depicts a fluorescence microscopy image of a *C. elegans* L4 larvae expressing mCherry::AnkB WT (SEQ ID NO: 3) driven by the col-19 promoter, which is specifically expressed in hypodermal cells from the young adult stage onwards (left panel) showing no expression of mCherry::AnkB WT (SEQ ID NO: 3) in the larval stage and no SQST-1::GFP aggregates (right panel).
FIG. 10I depicts a differential interference contrast microscopy image of a *C. elegans* wild embryo (left panel) and a fluorescence microscopy image showing fluorescence from SQST-1::GFP, which is weakly expressed and diffusely localized in hypodermis (right panel).
FIG. 10J depicts a fluorescence microscopy image of a *C. elegans* embryo expressing mCherry::AnkB WT (SEQ ID NO: 3) driven by the myo-3 promoter which drives muscle specific expression (left panel) and a fluorescence microscopy image showing a large number of SQST-1::GFP aggregates accumulate in the muscles (right panel).
FIG. 10K depicts a fluorescence microscopy image of a *C. elegans* embryo expressing mCherry::AnkB W1592R (SEQ ID NO: 11) driven by the myo-3 promoter which drives muscle specific expression (left panel) and a fluorescence microscopy image showing no SQST-1::GFP (right panel).
FIG. 10L depicts a differential interference contrast microscopy image of a *C. elegans* wild-type L4 larvae (left panel) and a fluorescence microscopy image showing fluorescence from SQST-1::GFP, which is weakly expressed and diffusely localized in hypodermis (right panel).
FIG. 10M depicts a fluorescence microscopy image of a *C. elegans* L4 larvae expressing mCherry::AnkB WT (SEQ ID NO: 3) driven by the myo-3 promoter which drives muscle specific expression (left panel) (SEQ ID NO: 3) and a fluorescence microscopy image showing SQST-1::GFP aggregates accumulate in the muscle cells (right panel).
FIG. 10N depicts a fluorescence microscopy image of a *C. elegans* L4 larvae expressing mCherry::AnkB W1592R (SEQ ID NO: 11) driven by the myo-3 promoter which drives muscle specific expression (left panel) results in no SQST-1::GFP aggregates in the muscle cells (right panel).
FIG. 10O depicts a differential interference contrast microscopy image of a *C. elegans* wild-type embryo and a fluorescence microscopy image showing fluorescence from SQST-1::GFP, which is weakly expressed and diffusely localized in hypodermis (right panel).
FIG. 10P depicts a fluorescence microscopy image of a *C. elegans* embryo expressing mCherry::AnkB WT (SEQ ID NO: 1) driven by the vha-6 promoter which drives intestines specific expression (left panel) a fluorescence microscopy image showing SQST-1::GFP aggregates accumulate in the intestine cells (right panel).
FIG. 10Q depicts a fluorescence microscopy image of a *C. elegans* embryo expressing mCherry::AnkB W1592R (SEQ ID NO: 11) driven by the vha-6 promoter which drives intestines specific expression (left panel) results in no SQST-1::GFP aggregates in the intestine cells (right panel).
FIG. 10R depicts a differential interference contrast microscopy image of a *C. elegans* wild-type larvae and a fluorescence microscopy image showing fluorescence from SQST-1::GFP, which is weakly expressed and diffusely localized in the cytoplasm (right panel).
FIG. 10S depicts a fluorescence microscopy image of a *C. elegans* larvae expressing mCherry::AnkB WT (SEQ ID NO: 1) driven by the vha-6 promoter which drives intestines specific expression (left panel) a fluorescence microscopy image showing SQST-1::GFP aggregates accumulate in the intestine cells (right panel).
FIG. 10T depicts a fluorescence microscopy image of a *C. elegans* embryo expressing mCherry::AnkB W1592R (SEQ ID NO: 11) driven by the vha-6 promoter which drives intestines specific expression (left panel) results in no SQST-1::GFP aggregates in the intestine cells (right panel).
FIG. 10U shows a survival curve for Pvha-6::ch::AnkB WT and Pvha-6::ch::AnkB WR worms. (Median lifespan: 18.87 days for Pvha-6::ch::AnkB WT and 18.13 days for Pvha-6::ch::AnkB WR; p=0.7585).
FIG. 10V shows a survival curve for Py37a1b.5::ch::AnkB WT and Py37a1b.5::ch::AnkB WR worms. (Median lifespan: 16.64 days for Py37a1b.5::ch::AnkB WT and 18.63 days for Py37a1b.5::ch::AnkB WR; p=0.0197).
FIG. 10W depicts a fluorescence microscopy image of a *C. elegans* L4 larvae expressing mCherry::AnkB WT (SEQ ID NO: 3) driven by the myo-3 promoter which drives muscle specific expression (left panel) (SEQ ID NO: 3) and a fluorescence microscopy image showing a small number of SQST-1::GFP aggregates accumulate in the muscle cells (right panel). Expression levels of AnkB WT peptide correlate with the degree of autophagy inhibition. Animals with weak expression level of Ch::AnkB WT contain few SQST-1::GFP aggregates in muscle cells, while the number of SQST-1::GFP aggregates is more in animals with high expression level of Ch::AnkB WT.
FIG. 10X depicts a fluorescence microscopy image of a *C. elegans* L4 larvae expressing mCherry::AnkB WT (SEQ ID NO: 3) driven by the myo-3 promoter which drives muscle specific expression (left panel) (SEQ ID NO: 3) and a fluorescence microscopy image showing a number of SQST-1::GFP aggregates accumulate in the muscle cells (right panel).) Expression levels of AnkB WT peptide correlate with the degree of autophagy inhibition. Animals with weak expression level of Ch::AnkB WT contain few SQST-1::GFP aggregates in muscle cells, while the number of SQST-1::GFP aggregates is more in animals with high expression level of Ch::AnkB WT.
FIG. 10Y depicts a fluorescence microscopy image of a *C. elegans* L4 larvae expressing mCherry::AnkB WT (SEQ ID NO: 3) driven by the myo-3 promoter which drives muscle specific expression (left panel) (SEQ ID NO: 3) and a fluorescence microscopy image showing a number of SQST-1::GFP aggregates accumulate in the muscle cells (right panel).) Expression levels of AnkB WT peptide correlate with the degree of autophagy inhibition. Animals with weak expression level of Ch::AnkB WT contain few SQST-1::GFP aggregates in muscle cells, while the number of SQST-1::GFP aggregates is more in animals with high expression level of Ch::AnkB WT.
Figure 10:
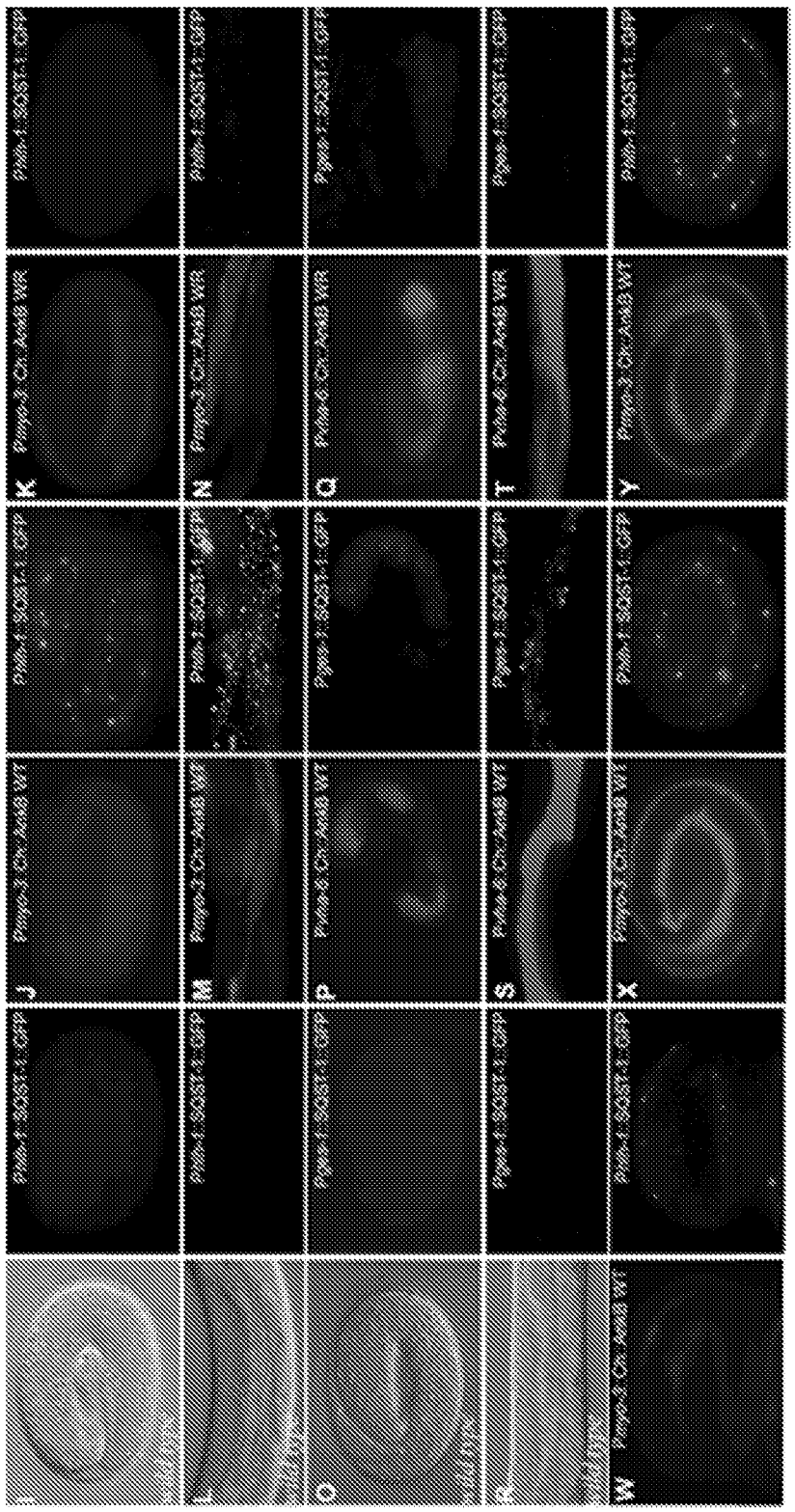
Figure 10:
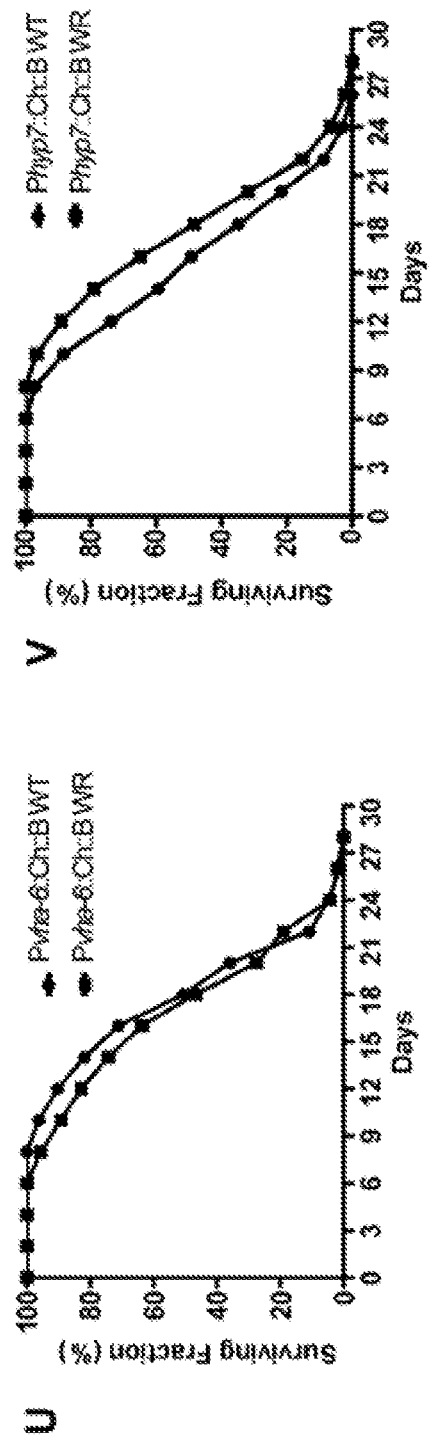

C. Tissue- and Temporal-Specific Depletion of Autophagy by Expression of the Ank-Derived Peptides Although a large collection of autophagy mutants were isolated from genetic screens (Tian et al., 2010), assays to inhibit autophagy activity in a spatiotemporal manner are not available. We investigated whether the AnkB peptide can block autophagy in a tissue- and temporal-specific manner. The AnkB peptide was expressed under the control of tissue-specific promoters, including the promoter of myo-3 for body wall muscle cells, y37A1B.5 for hypodermal cells and vha-6 for intestinal cells. The expression constructs were injected into animals carrying the corresponding tissue-specific SQST-1::GFP expression integrated lines. We found that a large number of SQST-1::GFP aggregates accumulated in animals expressing AnkB WT peptide in different tissues from the embryonic to adult stages, while animals expressing WR peptide showed no accumulation (FIG. 9A-F, FIG. 10I-T). The accumulation of SQST-1::GFP aggregates was also compared in animals with different expression levels of AnkB WT Animals with weak expression level of the AnkB WT peptide contained less SQST-1::GFP aggregates, and the level of SQST-1::GFP aggregates increases with increasing expression of the AnkB WT peptide (FIG. 10W-Y).

We also examined whether the AnkB peptide can impair autophagy in a temporal control manner. The expression of AnkB WT was driven by the promoter of col-19, which is expressed in hypodermal cells from the young adult stage onwards. We found that the animals expressing this peptide exhibited adult-specific accumulation of SQST-1::GFP aggregates phenotype, while no aggregates were found from the embryonic to L4 larval stages (FIG. 9G-I).

Autophagy is known to regulate the adult worm aging process. We found that worms expressing Pnfya-1::Cherry::AnkB WT dramatically shortened the life span compared to animals expressing Cherry::AnkB WR (FIG. 9J). Expressing Cherry::AnkB WT in muscle cells and intestinal cells did not significantly reduce the life span compared to animals expressing Cherry::AnkB WR (FIG. 9K, FIG. 10U). The autophagy defect caused by AnkB was weaker than that in autophagy mutants. Depleted autophagy activity in hypodermal cells by expressing Cherry::AnkB WT slightly reduced the mean life span (FIG. 10V). These results indicate that impairments of autophagy in different tissues contributes differentially to the aging in worms. Taken together, these results indicate that the AnkB peptide can inhibit autophagy activity in a spatial- and temporal-specific manner in *C. elegans*.

Figure 11:
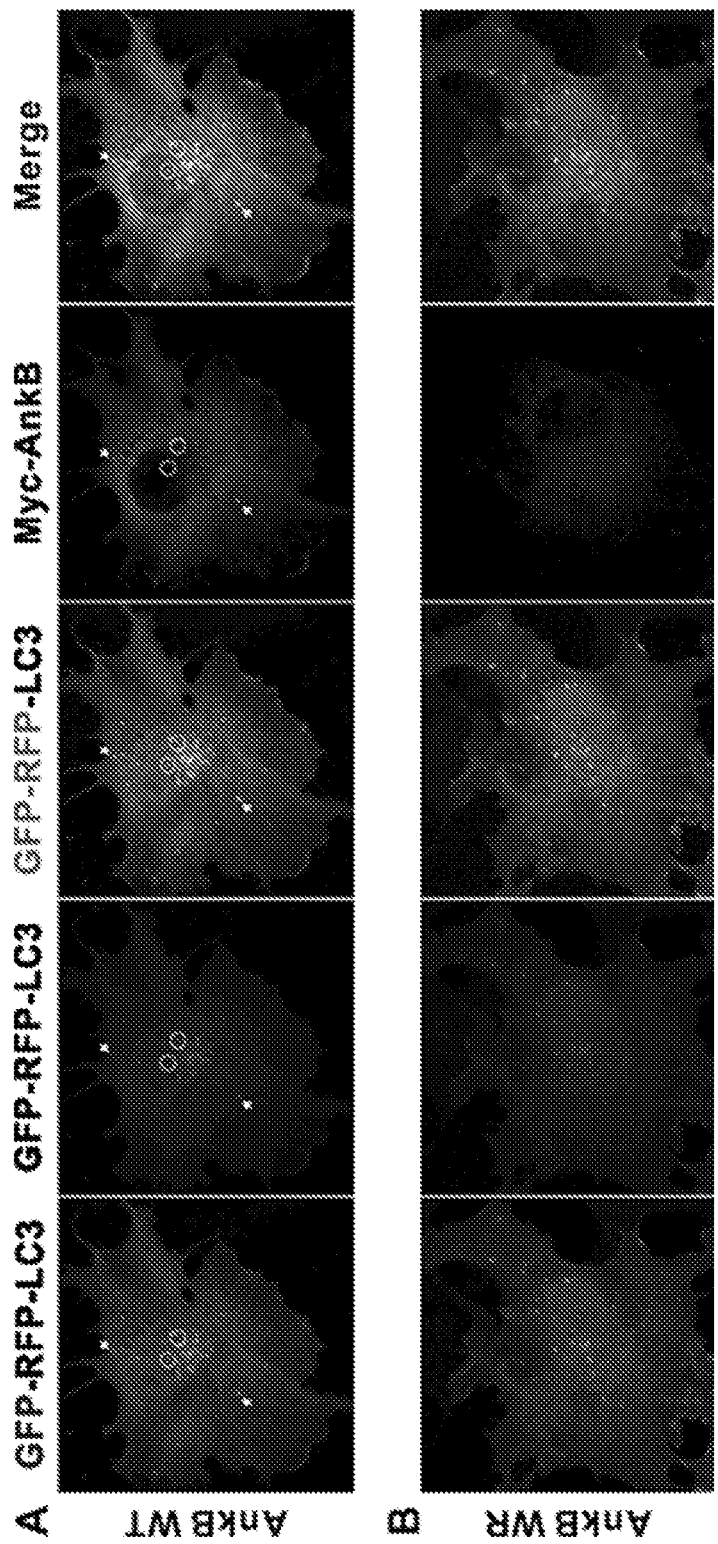
FIG. 11A depicts a fluorescence microscopy image of COS7 cells co-transfected with GFP-RFP-LC3B and Myc-AnkB WT (SEQ ID NO: 3) can act as an autophagosome marker. The arrows indicate the co-localization of the GFP-RFP-LC3B puncta and the Myc AnkB puncta; the red only signals are indicated with circles.
FIG. 11B depicts a fluorescence microscopy image of COS7 cells co-transfected with GFP-RFP-LC3B and Myc-AnkB W1989R (SEQ ID NO: 13) can act as an autophagosome marker. The arrows indicate the co-localization of the GFP-RFP-LC3B puncta and the Myc AnkB puncta; the red only signals are indicated with circles.

We next tried to explore the potential applications of the Ank-derived peptides as autophagosome markers. The COS7 cells were co-transfected with GFP-RFP-LC3B and Myc tagged AnkB WT or AnkB WR peptides. In such design, the LC3B on the autophagosome will exhibit both green and red fluorescence signal, while the LC3B on the lysosome will only show red fluorescence as GFP is quenched in the acidic environment. Since high amount of AnkB WT peptides expressed in the cell can effectively inhibit autophagy as we demonstrated above, we only focused on the COS7 cells with low expression level of Myc-AnkB. In the cells with AnkB WT expression, a significant number of yellow (green signal merged with red signal) and red only puncta are observed, suggesting that the autophagic flux remains normal in the presence of such low amount of AnkB WT peptides (FIG. 11A). LC3B are mainly localized on the autophagosome as vast majority of the puncta are both green and red (FIG. 11A). Myc-AnkB WT peptides are perfectly co-localized with these dual-color puncta but not the red only puncta (FIG. 11A). As a negative control, the AnkB WR peptides are diffused in the cells (FIG. 11B). The above observation suggested that low levels of AnkB WT can serve as an efficient and specific marker for the LC3B on the autophagosome.

REFERENCES

Altschul, S. F., Gish, W., Miller, W., Myers, E. W., and Lipman, D. J. (1990). Basic local alignment search tool. J. Mol. Biol. 215, 403-410.

Birgisdottir, A. B., Lamark, T., and Johansen, T. (2013). The LIR motif—crucial for selective autophagy. J. Cell Sci. 126, 3237-3247.

Bjorkoy, G., Lamark, T., Brech, A., Outzen, H., Perander, M., Overvatn, A., Stenmark, H., and Johansen, T. (2005). p62/SQSTM1 forms protein aggregates degraded by autophagy and has a protective effect on huntingtin-induced cell death. J. Cell Biol. 171, 603-614.

Cheng, X., Wang, Y., Gong, Y., Li, F., Guo, Y., Hu, S., Liu, J., and Pan, L. (2016). Structural basis of FYCO1 and MAP1LC3A interaction reveals a novel binding mode for Atg8-family proteins. Autophagy 12, 1330-1339.

Choi, A. M., Ryter, S. W., and Levine, B. (2013). Autophagy in human health and disease. N. Engl. J. Med. 368, 651-662.

Deng, Z., Purtell, K., Lachance, V., Wold, M. S., Chen, S., and Yue, Z. (2017). Autophagy Receptors and Neurodegenerative Diseases. Trends Cell Biol. 27, 491-504.

Galluzzi, L., Baehrecke, E. H., Ballabio, A., Boya, P., Bravo-San Pedro, J. M., Cecconi, F., Choi, A. M., Chu, C. T., Codogno, P., Colombo, M. I., et al. (2017a). Molecular definitions of autophagy and related processes. EMBO J. 36, 1811-1836.

Galluzzi, L., Bravo-San Pedro, J. M., Levine, B., Green, D. R., and Kroemer, G. (2017b). Pharmacological modulation of autophagy: therapeutic potential and persisting obstacles. Nat. Rev. Drug Discov. 16, 487-511.

Jiang, P., and Mizushima, N. (2014). Autophagy and human diseases. Cell Res. 24, 69-79.

Klionsky, D. J., Abdelmohsen, K., Abe, A., Abedin, M. J., Abeliovich, H., Acevedo Arozena, A., Adachi, H., Adams, C. M., Adams, P. D., Adeli, K., et al. (2016). Guidelines for the use and interpretation of assays for monitoring autophagy (3rd edition). Autophagy 12, 1-222.

Lee, Y. K., Jun, Y. W., Choi, H. E., Huh, Y. H., Kaang, B. K., Jang, D. J., and Lee, J. A. (2017). Development of LC3/GABARAP sensors containing a LIR and a hydrophobic domain to monitor autophagy. EMBO J. 36, 1100-1116.

Levine, B., and Kroemer, G. (2008). Autophagy in the pathogenesis of disease. Cell 132, 27-42.

Levine, B., Mizushima, N., and Virgin, H. W. (2011). Autophagy in immunity and inflammation. Nature 469, 323-335.

Manil-Segalen, M., Lefebvre, C., Jenzer, C., Trichet, M., Boulogne, C., Satiat-Jeunemaitre, B., and Legouis, R. (2014). The C. elegans LC3 acts downstream of GABARAP to degrade autophagosomes by interacting with the HOPS subunit VPS39. Dev. Cell 28, 43-55.

Maruyama, Y., Sou, Y. S., Kageyama, S., Takahashi, T., Ueno, T., Tanaka, K., Komatsu, M., and Ichimura, Y. (2014). LC3B is indispensable for selective autophagy of p62 but not basal autophagy. Biochem. Biophys. Res. Commun. 446, 309-315.

Menzies, F. M., Fleming, A., and Rubinsztein, D. C. (2015). Compromised autophagy and neurodegenerative diseases. Nat. Rev. Neurosci. 16, 345-357.

Mizushima, N., Yoshimori, T., and Levine, B. (2010). Methods in mammalian autophagy research. Cell 140, 313-326.

Mizushima, N., Yoshimori, T., and Ohsumi, Y. (2011). The role of Atg proteins in autophagosome formation. Annu. Rev. Cell Dev. Biol. 27, 107-132.

Noda, N. N., Ohsumi, Y., and Inagaki, F. (2010). Atg8-family interacting motif crucial for selective autophagy. FEBS Lett. 584, 1379-1385.

Olsvik, H. L., Lamark, T., Takagi, K., Larsen, K. B., Evjen, G., Overvatn, A., Mizushima, T., and Johansen, T. (2015). FYCO1 Contains a C-terminally Extended, LC3A/B-preferring LC3-interacting Region (LIR) Motif Required for Efficient Maturation of Autophagosomes during Basal Autophagy. J. Biol. Chem. 290, 29361-29374.

Pankiv, S., Clausen, T. H., Lamark, T., Brech, A., Bruun, J. A., Outzen, H., Overvatn, A., Bjorkoy, G., and Johansen, T. (2007). p62/SQSTM1 binds directly to Atg8/LC3 to facilitate degradation of ubiquitinated protein aggregates by autophagy. J. Biol. Chem. 282, 24131-24145.

Rubinsztein, D. C., Codogno, P., and Levine, B. (2012). Autophagy modulation as a potential therapeutic target for diverse diseases. Nat. Rev. Drug Discov. 11, 709-730.

Stolz, A., Putyrski, M., Kutle, I., Huber, J., Wang, C., Major, V., Sidhu, S. S., Youle, R. J., Rogov, V. V., Dotsch, V., et al. (2017). Fluorescence-based ATG8 sensors monitor localization and function of LC3/GABARAP proteins. EMBO J. 36, 549-564.

Tian, Y., Li, Z., Hu, W., Ren, H., Tian, E., Zhao, Y., Lu, Q., Huang, X., Yang, P., Li, X., et al. (2010). C. elegans screen identifies autophagy genes specific to multicellular organisms. Cell 141, 1042-1055.

Wu, F., Watanabe, Y., Guo, X. Y., Qi, X., Wang, P., Zhao, H. Y., Wang, Z., Fujioka, Y., Zhang, H., Ren, J. Q., et al. (2015). Structural Basis of the Differential Function of the Two C. elegans Atg8 Homologs, LGG-1 and LGG-2, in Autophagy. Mol. Cell 60, 914-929.

Zhang, H., Chang, J. T., Guo, B., Hansen, M., Jia, K., Kovacs, A. L., Kumsta, C., Lapierre, L. R., Legouis, R., Lin, L., et al. (2015). Guidelines for monitoring autophagy in Caenorhabditis elegans. Autophagy 11, 9-27.

What is claimed is:

1. A recombinant peptide comprising the amino acid sequence of SEQ ID NO: 1, wherein position 7, 12, 13 or 16 of SEQ ID NO: 1 is substituted with Arg or Gln, and wherein the peptide binds GABA Type A Receptor-Associated Protein (GABARAP).

2. The recombinant peptide of claim 1, wherein position 7 or 12 of SEQ ID NO:1 is substituted with Arg, or position 13 or 16 of SEQ ID NO:1 is substituted with Gln.

3. The recombinant peptide of claim 1, wherein position 7 or 12 of SEQ ID NO:1 is substituted with Arg.

4. The recombinant peptide of claim 1, wherein position 13 or 16 of SEQ ID NO:1 is substituted with Gln.

5. The recombinant peptide of claim 1, wherein the peptide comprises the amino acid sequence of SEQ ID NO:2.

6. The recombinant peptide of claim 5, wherein the peptide comprises the amino acid sequence of SEQ ID NO:14.

7. The recombinant peptide of claim 1, wherein the peptide comprises the amino acid sequence of SEQ ID NO:15.

8. The recombinant peptide of claim 1, wherein the peptide comprises the amino acid sequence of SEQ ID NO:16.

9. The recombinant peptide of claim 1, further comprising an affinity tag or detectable label.

10. The recombinant peptide of claim 9, wherein the detectable label is selected from the group consisting of chromogenic enzymes, radioactive isotopes, chromophores, luminescent compounds, fluorescent compounds, magnetic resonance imaging compounds, superparamagnetic particles, and ultra-small superparamagnetic particles.

11. A polynucleotide encoding the recombinant peptide of claim 1.

12. A method of inhibiting autophagy in a cell comprising the step of contacting the cell with the recombinant peptide of claim 1 thereby inhibiting autophagy in the cell.

13. The method of claim 12, wherein the peptide comprises the amino acid sequence of SEQ ID NO:2.

14. The method of claim 12, wherein the peptide comprises the amino acid sequence of SEQ ID NO:14.

15. The method of claim 12, wherein the peptide comprises the amino acid sequence of SEQ ID NO:15.

16. The method of claim 12, wherein the peptide comprises the amino acid sequence of SEQ ID NO:16.

17. The method of claim 12, wherein the cell is within a person's body.

* * * * *